US009579048B2

(12) United States Patent
Rayner et al.

(10) Patent No.: US 9,579,048 B2
(45) Date of Patent: Feb. 28, 2017

(54) ACTIVITY MONITORING SYSTEM WITH HAPTIC FEEDBACK

(71) Applicant: TreeFrog Developments, Inc., San Diego, CA (US)

(72) Inventors: Gary A. Rayner, Henderson, NV (US); James S. Nolan, San Diego, CA (US); David D. Bohn, Fort Collins, CO (US); Frederick J. Zimbric, Fort Collins, CO (US); Peter J. Gronewoller, Fort Collins, CO (US); Kyle M. Fanning, Fort Collins, CO (US); Travis W. Smith, Fort Collins, CO (US)

(73) Assignee: TreeFrog Developments, Inc, San Diego, CA (US)

( * ) Notice: Subject to any disclaimer, the term of this patent is extended or adjusted under 35 U.S.C. 154(b) by 333 days.

(21) Appl. No.: 14/077,387

(22) Filed: Nov. 12, 2013

(65) Prior Publication Data
US 2014/0228649 A1    Aug. 14, 2014

Related U.S. Application Data

(63) Continuation-in-part of application No. 13/954,910, filed on Jul. 30, 2013, now abandoned.
(Continued)

(51) Int. Cl.
*A61B 5/00* (2006.01)
*G06F 19/00* (2011.01)
(Continued)

(52) U.S. Cl.
CPC ............ *A61B 5/1118* (2013.01); *A61B 5/0002* (2013.01); *A61B 5/02055* (2013.01);
(Continued)

(58) Field of Classification Search
None
See application file for complete search history.

(56) References Cited

U.S. PATENT DOCUMENTS

| 3,184,847 A | 5/1965 | Leo |
| 4,097,878 A | 6/1978 | Cramer |

(Continued)

FOREIGN PATENT DOCUMENTS

EP    2289403 A1    3/2011

OTHER PUBLICATIONS

International Search Report for Application No. PCT/US2013/052789, mailed Jan. 8, 2014.

*Primary Examiner* — William Thomson
*Assistant Examiner* — Marie Archer

(57) ABSTRACT

An activity monitoring apparatus is provided. The activity monitoring apparatus includes a retention feature configured to removably secure the monitoring apparatus to a participant performing a physical activity. The activity monitoring apparatus further includes a clasping mechanism configured to receive a mobile electronic device and removably secure the mobile electronic device to the monitoring apparatus. The activity monitoring apparatus further includes a physiological data collector and electronic circuitry. The physiological data collector is configured to collect physiological data associated with the participant performing the physical activity. The electronic circuitry is configured to receive the physiological data associated with the participant from the physiological data collector, process the physiological data, and wirelessly transmit the processed physiological data to the mobile electronic device for display on the mobile electronic device.

16 Claims, 8 Drawing Sheets

Related U.S. Application Data

(60) Provisional application No. 61/677,450, filed on Jul. 30, 2012.

(51) Int. Cl.
*A61B 5/11* (2006.01)
*A61B 5/0205* (2006.01)
*A61B 5/024* (2006.01)

(52) U.S. Cl.
CPC .......... *A61B 5/6898* (2013.01); *A61B 5/7455* (2013.01); *G06F 19/3418* (2013.01); *G06F 19/3481* (2013.01); *A61B 5/0059* (2013.01); *A61B 5/024* (2013.01)

(56) References Cited

U.S. PATENT DOCUMENTS

| | | | |
|---|---|---|---|
| 4,420,078 A | 12/1983 | Belt et al. | |
| 5,541,813 A | 7/1996 | Satoh et al. | |
| 5,598,849 A | 2/1997 | Browne | |
| 6,068,119 A | 5/2000 | Derr et al. | |
| 6,585,622 B1 | 7/2003 | Shum et al. | |
| 7,158,376 B2 | 1/2007 | Richardson et al. | |
| 7,180,735 B2 | 2/2007 | Thomas et al. | |
| 7,251,454 B2 | 7/2007 | White | |
| 7,318,521 B2 | 1/2008 | Lau | |
| 7,519,327 B2 | 4/2009 | White | |
| 7,841,966 B2 | 11/2010 | Aaron et al. | |
| 8,033,959 B2 | 10/2011 | Oleson et al. | |
| 8,188,877 B2 | 5/2012 | Shum et al. | |
| 8,342,325 B2 | 1/2013 | Rayner | |
| 8,352,211 B2 | 1/2013 | Vock et al. | |
| 8,360,936 B2 | 1/2013 | Dibenedetto et al. | |
| 8,446,378 B2 | 5/2013 | Moll-Carrillo et al. | |
| 8,477,046 B2 | 7/2013 | Alonso | |
| 8,502,693 B2 | 8/2013 | Shum et al. | |
| 8,509,882 B2 | 8/2013 | Albert et al. | |
| 2002/0085342 A1 | 7/2002 | Chen et al. | |
| 2006/0047447 A1 | 3/2006 | Brady et al. | |
| 2006/0122474 A1 | 6/2006 | Teller et al. | |
| 2007/0261978 A1 | 11/2007 | Sanderson | |
| 2007/0299330 A1* | 12/2007 | Couronne | A61B 5/02416 600/368 |
| 2008/0096726 A1 | 4/2008 | Riley et al. | |
| 2008/0275309 A1* | 11/2008 | Stivoric | A61B 5/411 600/300 |
| 2009/0017884 A1 | 1/2009 | Rotschild | |
| 2009/0047645 A1 | 2/2009 | Dibenedetto et al. | |
| 2009/0084705 A1* | 4/2009 | Justiss | A45F 5/02 206/724 |
| 2009/0174558 A1 | 7/2009 | White | |
| 2009/0291726 A1 | 11/2009 | Svensson | |
| 2010/0152545 A1* | 6/2010 | Ramsay | A61B 5/0002 600/301 |
| 2010/0185398 A1 | 7/2010 | Berns et al. | |
| 2011/0054272 A1 | 3/2011 | Derchak | |
| 2011/0298613 A1* | 12/2011 | Ben Ayed | A61B 5/002 340/539.11 |
| 2012/0015779 A1 | 1/2012 | Powch et al. | |
| 2012/0116550 A1 | 5/2012 | Hoffman et al. | |
| 2012/0251079 A1 | 10/2012 | Meschter et al. | |
| 2012/0254934 A1 | 10/2012 | McBrearty et al. | |
| 2012/0283855 A1 | 11/2012 | Hoffman et al. | |
| 2013/0220841 A1 | 8/2013 | Yang | |
| 2013/0310658 A1* | 11/2013 | Ricks | A61B 5/1118 600/301 |

* cited by examiner

ACTIVITY MONITORING SYSTEM WITH HAPTIC FEEDBACK

CROSS-REFERENCE TO RELATED APPLICATIONS

This application is a continuation in part of application Ser. No. 13/954,910, filed Jul. 30, 2013, which claims the benefit of U.S. Provisional Patent Application No. 61/677,450, filed Jul. 30, 2012, both of which are hereby incorporated by reference in their entirety.

BACKGROUND

Athletes and persons wishing to monitor their health often desire to obtain or monitor data pertaining to their physical activities, accomplishments, or condition. In some situations, a physician may prescribe certain steps or exercise to be performed by a patient under certain conditions, such as performing an exercise at or near a certain heart rate. The doctor and/or the patient may wish to gather data regarding the performance of the exercise, the conditions under which the exercise was performed, and/or how the patient is responding to the exercise. An athlete may wish to gather and monitor details about his or her physical performance in a similar manner. For example, an athlete who can correlate different training or exercise techniques with improved performance metrics can become faster, stronger, or exert more force in an action, such as hitting a ball harder. Athletes, patients, and anyone else associated with a physical activity can benefit from improved techniques for gathering, monitoring, correlating, analyzing, using, interpreting, and making decisions based on physical activity data

SUMMARY

One or more electronic devices can be used to measure any number of conditions relating to participation in a physical activity and to process the measurements to generate a data output providing a useful representation of the measured conditions. These representations can be further processed to generate trends, maximums, minimums, and/or statistical information related to the performance of the physical activity. In order to accomplish these and other objectives, apparatuses, systems, and methods for determining a set of characteristics of a participant performing an activity is provided.

In one example, an activity monitoring apparatus is provided. The activity monitoring apparatus includes a retention feature configured to removably secure the monitoring apparatus to a participant performing a physical activity. The activity monitoring apparatus further includes a clasping mechanism configured to receive a mobile electronic device and removably secure the mobile electronic device to the monitoring apparatus. The activity monitoring apparatus further includes a physiological data collector and electronic circuitry. The physiological data collector is configured to collect physiological data associated with the participant performing the physical activity. The electronic circuitry is configured to receive the physiological data associated with the participant from the physiological data collector, process the physiological data, and wirelessly transmit the processed physiological data to the mobile electronic device for display on the mobile electronic device.

In another example, a system includes two or more data collectors and a processor. The two or more data collectors include a physical data collector for collecting physical data associated with the activity and a physiological data collector for collecting physiological data associated with the activity. The processor has one or more data inputs in communication with the processor. Each of the one or more data inputs communicates with at least one of the data collectors to receive the physical data or the physiological data. The processor is adapted to receive the physical data and the physiological data from the one or more data inputs and process the physical data and the physiological data according to a characteristic generation program. The set of characteristics represents a performance level of the participant performing the physical activity.

In yet another example, a system includes a data processing system and a viewing system. The data processing system receives physical data and physiological data from data collectors associated with activity participants. The data collectors include at least one physical data collector for collecting physical data associated with the activity and at least one physiological data collector for collecting physiological data associated with the activity. The data processing system is adapted to process the physical data and the physiological data according to one or more characteristic generation programs to determine a set of characteristics. The set of characteristics represents a performance level of the participants. The viewing system is coupled with the data processing system via a communications network. The viewing system generates a graphical representation of the set of characteristics for the participants for display on a graphical user interface.

DETAILED DESCRIPTION

Figure 1:
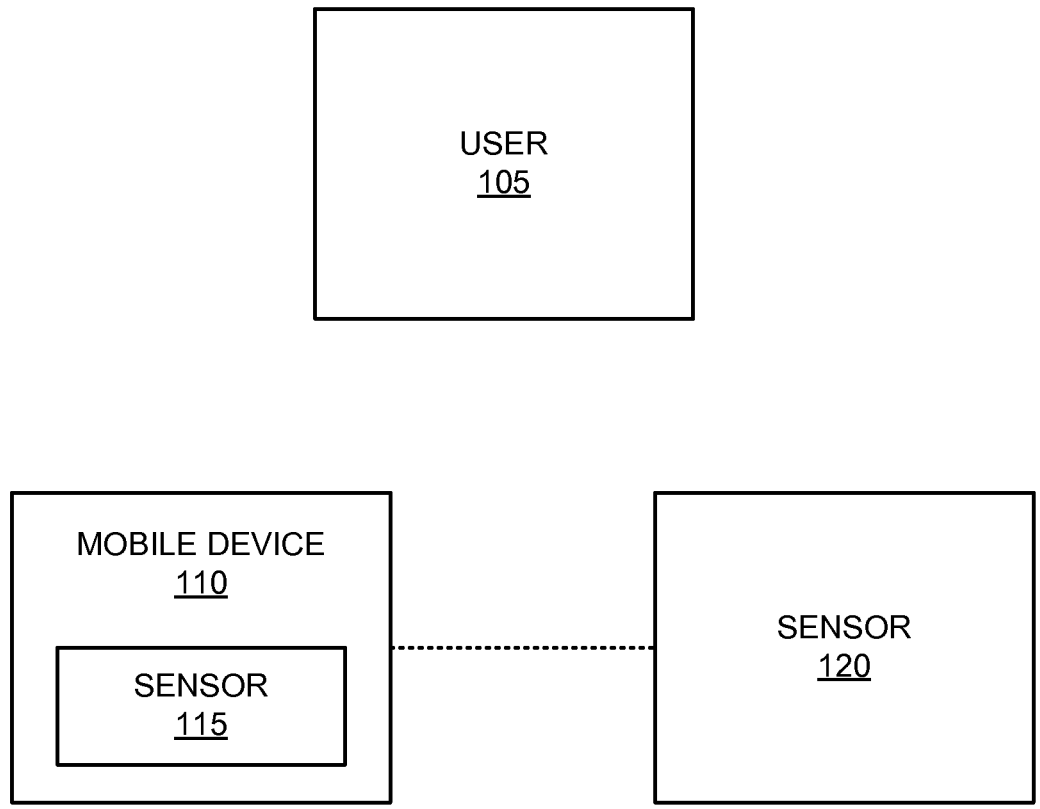
FIG. 1 illustrates devices for monitoring of a physical activity.

Devices for tracking physical exertion and physiological condition such as pedometers, heart rate monitors, stopwatches, and the like, can be cumbersome for a participant in an activity or event to utilize, especially if multiple devices are being used at the same time. Described herein are apparatuses, devices, systems, and methods for gathering, monitoring, correlating, analyzing, using, interpreting, and/or making decisions based on physical activity data. Also described are apparatuses, devices, systems, and methods for utilizing the physical activity data to derive further information about the participant's exertion or physiology. The apparatuses, devices, systems, and methods are primarily described with respect to a smartphone. However, it should be appreciated that the disclosed techniques may be used with any suitable electronic device.

The types of situations in which a person could want to record data regarding performance of an activity vary. A person, or participant, could wish to monitor his or her improvement in the execution of an activity or event over time, such as over days, weeks, or months of training. A person can also desire to record that he or she is involved in any type of activity and correlate that activity to physiological parameters, such as heart rate, blood pressure, blood glucose levels, cholesterol levels, and the like, to monitor his or her general health. In addition, a person may want to monitor physiological parameters and improvement in the execution of an activity or event over time, for example, to verify the effects of a change in diet and/or training regimes.

While the techniques disclosed herein are discussed primarily with respect to physical activities, the same techniques may also be applied to mental activities. For example, a participant may be a participant in an activity that requires mental focus or performance and the techniques disclosed herein may be used for gathering, monitoring, correlating, analyzing, using, interpreting, and making decisions based on mental activity or performance data. In some cases, the techniques may be applied to activities having both mental and physical elements.

A participant in a sport or other physical activity may wish to monitor his or her exertion or level of participation in activities on land, in the water, with or without the use of machines or other accessories. Activities on land without the use of machines can include walking, jogging, running, calisthenics, bodyweight exercise, stretching, yoga, dancing, martial arts, and the like. Bicycling, roller skating, skate boarding, snowboarding, running hurdles, rock climbing, pole-vaulting, bungee jumping, sky-diving, javelin throwing, hammer throwing, skiing, tennis, baseball, cricket, soccer, football, rugby, rappelling, horseback riding, vehicle racing, archery, fencing, gymnastics, basketball, hockey, ice skating, mountaineering, ice climbing, lacrosse, Frisbee®, golf, bowling, weight lifting, and the like can be activities on land that utilize machines or other accessories. Activities in the water can include swimming, sailing, surfing, paddling, water aerobics, diving, kite boarding, windsurfing, water-skiing, and the like. The techniques described herein may be applied to various other activities involving physical and/or mental performance.

In order to monitor a participant's exertion or level of performance in an activity or event, various types of sensors or data collection devices can be used. Sensors that can be used include a clock, a timer, a stop watch, a motion sensor, a speed sensor, a pedometer, a cadence sensor, an accelerometer, a power meter, a mass sensor, an inertia sensor, a wind resistance sensor, a rolling resistance sensor, a pressure sensor, a strain gauge, a hear rate monitor, a thermal sensor, a compass, a magnetic sensor, a gravity sensor, a gyroscope, a global navigation satellite system (GNSS) receiver, a global positioning system (GPS) receiver, an altitude sensor, a humidity sensor, an acoustic sensor, a photo detector sensor, and the like. Other types of sensors or data collectors are possible and the techniques disclosed herein are not to be limited to any particular type of sensor or data collector.

Many different types of sensors or data collection devices may be used to capture data related to performance of an activity. The data may fall into categories of physiological data, physical data, and/or environmental data. Physiological data is data related to the state, condition, or functioning of one or more aspects of the participant's body. Physical data relates to a measurement of some other parameter related to performance of the physical activity such as a measurement of motion, speed, force, movement, location, distance, weight, and/or time. Physical data may also include measurement of a state or a condition of a piece of equipment or measurement of an environmental parameter. An environmental parameter may include some characteristic of the environment the activity is being performed in such as temperature, humidity, air quality, presence of dangerous chemicals, or noise level.

The various types of physiological sensors that can be used to monitor the physiological condition of a participant include heart rate monitors, blood pressure monitors, oxygen saturation monitors, hemoglobin sensors, $CO_2$ monitors, blood glucose meters, pulse oximeters, thermal (e.g., temperature) sensors, breathing rate monitors, electroencephalographic sensors, electrocardiographic sensors, and the like. Thermal sensors can include a thermocouple, an infrared (IR) thermal sensor, and/or other temperature sensing technology.

Heart rate may be measured non-invasively using seismocardiographic techniques, electrocardiographic techniques, or optical techniques (such as with a pulse oximeter). Combinations of any two of the techniques or all three may also be used. For example, seismocardiography (SCG) of an athlete can measure movement of the chest area from one or more accelerometers placed on the clavicle and/or sternum of an athlete to measure movement of the chest area with each heartbeat. Electrocardiography (ECG) techniques utilize an array of skin sensors in the chest area and/or limbs to detect skin depolarization for each heartbeat. The sensor array may be adhered to the chest area individually or as a unit. In some embodiments, the sensor array may be woven into a textile as part of a shirt, armband, sock, or other garment worn by the athlete. In some embodiments, a sensor or sensor array integrated or woven into a textile may be associated with a releasable adhesive that maintains its position on the athlete. In some embodiments, the sensor or sensor array may be integrated with a portion of a textile that has additional elasticity to aid maintenance of its position on the user (e.g., an elastic band integrated into a shirt or sock). An ECG sensor or sensor array may determine not only heart rate, but normal and abnormal aspects of the cardiac cycle, such as a P wave, QRS cycle, T wave, U wave, and/or the intervals between them. In certain embodiments, an ECG sensor or sensor array and an SCG sensor or sensor array can be utilized in tandem to send heart-related data to a mobile device, thus increasing accuracy (see, e.g., Castiglioni et al., Wearable Seismocardiography, Engineering in Medicine and Biology Society, 2007. EMBS 2007. 29th Annual International Conference of the IEEE, Abstract, incorporated herein by reference in its entirety).

In some cases, data may also be gathered using one or more neuroimaging techniques. For example, data may gathered using one or data collectors based on techniques such as: computed tomography (CT) computed axial tomography (CAT), diffuse optical imaging (DOI), diffuse optical tomography (DOT), event-related optical signal (EROS), magnetic resonance imaging (MRI), magnetoencephalography (MEG), positron emission tomography (PET), single-photon emission computed tomography (SPECT), and/or other neuroimaging techniques.

Optical detection of blood volume changes and blood oxygenation (e.g., using a pulse oximeter) may also be used to determine an athlete's heart rate, as well as other characteristics of arterial blood, such as blood pressure and oxygen saturation. Pulse oximeters utilize a light source (such as a light emitting diode) that shines light at multiple wavelengths through a thin tissue (such as a fingertip or earlobe) and into a photodetector. The ratio of absorbance or reflectance of the light wavelengths is used to non-invasively detect the level of oxygen-bound hemoglobin in blood and provide the saturation level of peripheral oxygen ($SpO_2$). Fluctuations in the signal due to changes in blood volume are used to detect pulse rate and eliminate signals from non-arterial tissues.

Photoplethysmography (PPG) is a simple optical technique that can be used to detect blood volume changes in the micro vascular bed of tissue. It may be used to non-invasively to make measurements at the skin surface. In some applications, a PPG waveform includes a pulsatile physiological waveform attributed to cardiac synchronous changes in the blood volume with each heartbeat and is superimposed on a slowly varying baseline signal with various lower frequency components attributed to respiration, sympathetic nervous system activity, and thermoregulation.

Capnographic detection of the partial pressure of $CO_2$ in an athlete's lung exhalations may be used to evaluate respiratory function in athletes and to retrain athletes in breathing to maximize performance. Nasal cannula may be used to sample lung exhalations and detect $CO_2$ levels via absorbance of an IR wavelength by carbon dioxide. Exemplary nasal devices are made by Oridion Capnography, Inc, Bedford, Mass., a subsidiary of Covidien, Inc.; see e.g., "Technical Note; MICROSTREAM Capnography", 2008, Oridion Capnography Inc., incorporated herein by reference in its entirety. Capnographic detection of carbon dioxide levels can allow detection of maximal oxygen consumption ($VO_2max$) by an athlete as a measure of fitness, especially in endurance sports.

In certain embodiments, the respiratory rate can be detected by using an acoustic sensor attached to the throat to detect turbulent airflow during breathing (e.g., RRa acoustic sensor RAS-125, Masimo Corp, Irvine, Calif. USA; see also U.S. Pat. No. 5,143,078, incorporated herein by reference in its entirety). Respiratory rate may also be detected using changes in humidity during breathing, using sensors in a mask or mounted on a lip of a person (see, e.g., WO 2008122806, incorporated herein by reference in its entirety).

Body fat levels can be measured using bioelectrical impedance between electrodes placed on the body, and can be utilized in calculations of fitness. Bioelectrical impedance can also measure increases and decreases in hydration levels as the athlete is training or competing, because the impedance changes with respect to increases and decreases in hydration. Body fat measurement may also be obtained optically by measuring the absorption and reflection of near IR light by tissue at one or more sites on the body (such as the bicep).

Myoelectric electrodes placed on the skin proximate one or more muscles of interest may be used to detect muscle activity. Two skin electrodes may be adhered proximate the muscle (e.g., a bicep, tricep, quadracep, or other muscle) to detect a voltage difference in the skin, with a third electrode placed away from the muscle for subtracting signal noise.

Electroencephalographic (EEG) or hemoencephalographic (HEG) sensors placed on the skin proximate brain regions of interest may also be used to detect and analyze brain activity using the technology disclosed herein. EEG sensors detect electrical changes in neural activity through the skin, while HEG uses near IR light to examine changes in blood flow in a given brain region, which indicate changes in metabolic rate of that brain region. EEG/HEG data may be used in conjunction with feedback mechanisms (e.g., auditory, visual, or haptic) to produce neurofeedback mechanisms and overcome issues such as concentration, fear, or the like.

In some implementations, an electrochemical sensor is used to analyze secretions and body fluids from an athlete. The electrochemical sensor may take in body fluids (e.g., blood, saliva, perspiration, or tears) from the athlete via capillary action into a microfluidic device and electrochemically detect one or more components of the secretion. Alternatively, the electrochemical sensor may be integrated with a woven or nonwoven material (e.g., textile or felt) or wearable polymer (e.g., Gore-Tex® or neoprene). An electrochemical sensor may detect the presence, absence, or amounts of biomarkers such as cells, lipids, carbohydrates, mineral salts, trace metals, amino acids, proteins, nucleic acids, dissolved gases, drugs or drug metabolites, or other chemical compounds in the body fluids of the athlete. The sensor may utilize polymerase chain reaction to amplify nucleic acid components of the secretion. The sensor may include nucleic acids (e.g., single stranded nucleic acids or aptamers), proteins, or other compounds to detect specific analytes in the secretions. For example, blood levels of glucose, lactate, and/or cholesterol may be measured.

In some cases, physiological measurements can be made using techniques such as photoplethysmography wherein optical or electromagnetic energy from one or more sources is directed toward the skin of the user and analyzing the characteristics of the reflections and/or scattering of that energy. More specifically, certain physiological measurements regarding blood flow may be made by detecting and analyzing the characteristics of the reflection of the energy from two or more different areas of the skin. In some cases, the reflections from the two or more different areas may have different characteristics because the areas have different blood vessel, vein, or artery concentrations or densities. In some situations, the optical scattering may also be analyzed to measure metabolites.

In some implementations, reflections based on different wavelengths of energy may be detected for comparison purposes. In some cases, one of these signals is subtracted from the other. This subtraction, as well as other signal conditioning or processing, may be performed by dedicated circuitry associated with the sensors performing the measurement, may be performed by a mobile electronic device to which the data is transmitted, or may be performed by a remote computer, including combinations thereof. Such subtraction and/or signal processing can be used to distinguish spurious or artifactual signals ("noise") from the energy signal of interest. These artifactual signals may be inherent properties of the skin or tissue being analyzed, or be signal variance caused by movement or vibration of the physiological sensors on the body. Thus, energy detectors (such as optical detectors) used to detect artifactual signals due to movement may be used as motion sensors. In order to detect and remove signal variance caused by physical movement or displacement of the physiological sensors, the energy sources and detectors should be in close proximity in order to correlate and/or remove the noise created by spurious movement of the sensor on the body.

In some cases, the energy source(s) may be one or more light emitting diodes, organic light emitting diodes, laser diodes, incandescent lamps, arc sources, micro-plasma sources, or combinations thereof. When using optical sources, the energy detectors may include photodiodes, avalanche photodiodes, photomultipliers, and/or other types of optical detectors. In some situations, measurements may also be made using acoustical energy, mechanical energy, electrical energy, and/or thermal energy. The source(s), detector(s), and other components described herein may be integrated into a single sensing module. The sensing module may be positioned in contact with the skin or in close proximity to the skin of the user in the form of a wearable device.

Motion sensors can include sensors that detect instantaneous motion and/or sensors that detect velocity. Instantaneous motion sensors can include accelerometers, gyroscopes, strain gauges, piezoelectric sensors, optical sensors, energy sensor, and the like for measurement of short duration movements or impulses. Sensors that detect velocity or speed can include those that utilize information about distances and passage of time. Sensors or data from sensors may be used in combination in some cases. Examples of such sensor combinations can include a calibrated pedometer and a stopwatch or a GPS receiver and a clock, a timer, a stopwatch, and/or a pendulum. Distance sensors can include pedometers, GPS receivers, sensors that utilize wireless signals to determine position such as cell phone tower signals used with a suitable device, and the like.

Sensors that can indicate the position of a participant, and possibly relative position of limbs or portions of the participant's body, are also useful in monitoring exertion or performance. Such sensors can include accelerometers, including multi-axis accelerometers, gyroscopes, GPSs, sensors that detect distance from a fixed object through electromagnetic detection, optical detection, sonic detection, and the like. Accelerometers and gyroscopes may be MEMS-based, nano-scale based, piezoelectric, piezoresistive, and the like. Combining these position sensors with a time marking sensor, such as a clock or timer, can help a person observe how his or her actions vary over a single event, such as an hour-long race or competition, or over a period of time such as over a training cycle that may last days, weeks, or months.

Extremes of heat, humidity, and altitude can affect athletic performance. Thus, sensors that detect changes in the immediate environment of an athlete may also be employed in technology disclosed herein. Temperature sensors, altimeters, wind sensors, humidity sensors, air quality sensors, and the like can collect data regarding the immediate environment of the athlete. This environmental data can be integrated with physiologic data of the athlete for an analysis of potential future performance, as well as warn the athlete of physiologic parameters that will reduce performance given the external environmental data.

Exertion sensors can also be useful to a participant wishing to track his or her performance over an event or training cycle. Such sensors include power meters, ergometers, mass indicators, motion detectors, cadence meters, pedometers, inertia sensors, wind resistance sensors, water resistance sensors, rolling resistance sensors, and the like. Some of these sensors can be used with devices that mark the passage of time, as described above.

The sensors described herein can be used with any mobile or handheld electronic device that is suitable for the activity a participant wishes to pursue. The sensors can be an integral part of such a handheld device or can be separate from the handheld device and relay data signals to the handheld device. In some implementations, the handheld electronic device can be a cellular phone, a smart cellular phone, a smartphone, a dedicated electronic device, an MP3 player, an ebook reader, an electronic organizer, a GPS receiver, a two-way radio, a multi-media device, a tablet computing device, a notebook computer, or the like. In some implementations, the handheld electronic device is used with a case, enclosure, or cover that allows the handheld electronic device to be used in challenging conditions. Challenging conditions can include, but are not limited to, those that expose the device to: water, precipitation, humidity, extreme temperatures, vibration, dirt, dust, sand, soil, mud, abrasion, shock, and/or impact (see U.S. Pat. No. 8,342,325, incorporated herein by reference in its entirety).

The data provided by sensors inherent or internal to the electronic handheld device can be augmented with data provided by one or more external sensors. The one or more external sensors may be placed on the body of the participant, located in the environment in which the participant's activity or event takes place, and/or attached to a piece of equipment used by the participant. The data can be agglomerated by a computer software application (an "app" on the handheld device and stored on the handheld device. The data can also be processed on the handheld device so that a participant can see his or her progress in terms meaningful to him or her, such as increases in speed, strength, endurance, or accuracy or improved health conditions or metrics, such as lower blood pressure. The data can also be shared with external devices or software programs. Such data sharing can occur over the air through wireless connections, through physical connections of the handheld device to an external device or network, or through a combination of wireless and physical connections. Shared data can be used by a coach, trainer, physician, or other interested party. In some situations, one or more access control processes may be used to control who is permitted to access the data or who receives the data.

In addition to gathering data with respect to a physical activity, data may also be fed back to an athlete, physical activity participant, or to another party. Feedback can be in the form of sensory feedback, such as for example visual feedback, auditory feedback, haptic feedback, or tactile feedback. Input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In some implementations, a user interface in at least one of the controlling device and the location and/or status monitoring device may provide notifications to an athlete of a change in the environment (e.g., geolocation, temperature, etc.) reported from a location, control, and status monitoring device, or in the status of one or more the athlete. The notification may be a visual signal, such as one or more (light emitting diodes) LEDs or other light sources. Multiple light sources may be used that flash in a specified sequence, multiple light colors, or the one or more light sources may modulate their intensity depending on the notification that needs to be communicated to the user. In some implementations, the notification may be an audio signal. The audio signal may be one or more audible, ultrasonic, or subsonic frequencies. The audio signal may vary in amplitude or duration. In some implementations, the sonic frequencies emitted may be a representation or recording of a human voice, an animal sound, such as a dog bark, or some other recorded sound. In some implementations, the notification may be a tactile or haptic signal.

Tactile or haptic signals are another type of signal output that can be created by the controlling devices, as well as location and/or status monitoring devices of the instant technology in response to a predetermined movement or change in the environment. The amplitude, timing, and duration of the haptic signal can be varied to indicate to a user the nature of the changed input. For example, a controlling device can vibrate in response to a data signal from a monitoring device when an athlete is within a certain range of a target distance, target location, target time, physiologic characteristic (e.g., heart rate for a specified time period, breath rate, or number of footfalls or strokes), or combination thereof. Similarly, the controlling device, as well as the location and/or status monitoring device can be configured to vibrate to alert an athlete that they are out of range from a target distance, target location, target time, physiologic characteristic (e.g., heart rate for a specified time period, breath rate, or number of footfalls or strokes), or combination thereof.

The haptic signals can include mechanical stimulation, vibration, and/or direct electric discharge. Direct electric discharge can be a low current discharge that is detected on the skin, or a higher discharge that causes physical discomfort. Haptic actuators can include, but are not limited to, vibrating motors, electrically conductive surfaces coupled with a charge creator, subsonic sound waves, electroactive polymers, piezoelectric actuators, electrovibration actuators (e.g., indirect charge actuators such as TeslaTouch®) and the like.

In some cases, it may desirable to know a participant's geolocation at any particular time during an athletic event. A coach or participant may also wish to retrospectively examine the participant's geolocation at regular intervals throughout the event. Consistent with one or more implementations of the current subject matter, the mobile device may receive data from a corresponding location device indicating such geolocation. In such cases, the location device may employ location sensors, receivers, or transceivers. Such location sensors can optionally include one or more technologies such as GNSS. Exemplary GNSS systems that enable accurate geolocation can include GPS in the United States, Globalnaya navigatsionnaya sputnikovaya sistema (GLONASS) in Russia, Galileo in the European Union, and BeiDou System (BDS) in China. Wireless signals from any signal emitter having a known location may be received and used for calculating location.

Of particular use are signals that themselves include location information or a unique identifier that can be indexed to a known location. For example, alternatively or in addition to navigation satellite information, location sensors consistent with this disclosure can include radio frequency (RF) and/or microwave power sensors, such as heat-based (thermistor or thermocouple power sensors) or diode detector sensors. RF and microwave power sensors can allow RF triangulation with respect to known-location transmitters such as cellular communication relay locations (e.g., cell towers), or other devices with known positions. Such signals, for example, may be based on the Institute of Electrical and Electronics Engineers' (IEEE) 802.11 standards (WiFi), IrDA (Infrared Data Association), ZigBee® (communications based upon IEEE 802 standard for personal area networks), Z-wave, wireless USB, or the like, and may include an identifier such as a Media Access Control (MAC) and/or Internet Protocol (IP) address of the transmitting device, or other typically unique identifier.

Other exemplary RF and microwave signal sources that may be used by a location device for determining location or proximity include RF signals from radio and television stations, as well as wireless utility meters for electricity, gas, or water can also be used. For example, a location device may receive signals from two or more transmitting devices, where the signals include an identifier for the transmitter (e.g., Media Access Control (MAC) address), from which an absolute location of the transmitter can be determined by lookup. Analysis of the two or more signals can then be performed to calculate a location of the location device. In some examples, a location device may include a processing unit that coordinates determination of the location of the device, such as using RF fingerprinting of one or more RF signal generators. The processing unit may also facilitate synchronization between a location device and a mobile device, as well as between a location device and a server or central hub.

RF fingerprinting of radio frequency or microwave signals from an RF source can allow for more accurate triangulation by accurately identifying RF or microwave emitting sources having known locations. In some implementations, multiple sensors for multiple types of RF or microwave signals can be used to identify and triangulate an accurate location. Geolocation can be correlated with an RF fingerprint of multiple RF or microwave sources, and known correlations of RF fingerprints and geolocations can be stored in a database. When RF or microwave signals from multiple sources are received by location sensors on a participant, the RF fingerprint can be determined and compared with the database in order to determine the geolocation of the user or athlete. The database may be stored on the mobile device or on another computing device.

In certain embodiments, RF signal analysis may be used for geolocation and/or proximity to fixed position relays and other athletes, and may include measurement of the received signal strength (or amplitude) of the radio signal. In some implementations, proximity of a device can be determined by reference to an object, such as another location device, a controlling device (such as mobile smartphone), or a fixed relay receiver or transceiver. For example, a Bluetooth® Smart signal from a location and status monitoring device may be analyzed to detect an approximate distance and direction from a controlling device. In another example, proximity may be obtained using Doppler principles. For example, a transceiver attached to the athlete may send a radio signal from the athlete to an object having a known location. The radio signal is then reflected from the object back to the transceiver. The returning RF waveforms are detected by matched-filtering, and delay in the return of the RF waveform is measured in order to determine distance from the object. In another example, a magnetic or electric field may be analyzed to detect disturbances in the field caused by movement of a relatively large dielectric object (such as a person, bicycle, or other sports equipment). Sensors can passively (and thus at low power) detect changes in spatial potential within the field and thus provide position, movement, and direction within the field. Low power communication devices (e.g., Bluetooth® Low Energy/Smart (BLE), ANT+, RFID, IrDA, Zigbee®, etc.) may be used, with or without an additional higher power communication device.

Synchronization or association of the controlling device with other devices may include an exchange of electronic data. The exchange of electronic data may notify an associated device (e.g., controlling device such as a smartphone) of a unique identifier for each of the other devices, or may provide a code shared in common by all of the associated devices. Devices may use unique identifiers to individually communicate with any or all of several associated location devices, and may obtain device-distinguishable data from each associated location device. On the other hand, when all devices share a common code for identification, the controlling device may treat a group of location devices as a single unit. In such implementations, a controlling device may learn of proximity or location from any one of the associated location devices. This may be useful and efficient in instances where all of the associated devices are typically considered together, such as a team of athletes that move together (e.g., a team of bicycle riders).

Implementations consistent with this disclosure may combine the use of unique identifiers and common codes in order to make use of the advantages of both schemes. A common code may alternatively be used to uniquely secure communications between the controlling device and location and status monitoring device(s). For example, a common code/password/key/token may be used as a part of an encryption scheme such as wireless access protocol (WAP), wired equivalent privacy (WEP), Wi-Fi Protected Access (WPA), variants thereof, or other standard or proprietary security protocols permitting secured communications. Such security protocols may implement cryptography algorithms such as advanced encryption standard (AES), data encryption standard (DES), RSA, and the like. In addition, communications may implement compression algorithms and/or hashing functions in order to reduce the amount of data transferred and to ensure data integrity. The encryption schemes may be implemented using dedicated circuitry and/or general purpose processors, and may further utilize processors, magnetic and/or solid state memory devices, electronic fobs, electronic dongles, SIM cards and the like, or any combination thereof.

Geolocation can also be determined by using inertial sensors (e.g., accelerometers and gyroscopes) either in addition to, or in place of GNSS, RF fingerprinting, or other location systems. If suitable RF or microwave signals are not available or have insufficient strength for detection, information from inertial sensors associated with the athlete can be used to calculate relative location using dead reckoning with respect to a previous location, or absolute location with respect to a last-known absolute location. As known by those of ordinary skill in the art, inertial sensor data on the current angular velocity and the current linear acceleration of an object may be used to determine the angular velocity and inertial position of a device having such sensors. In some implementations, inertial sensors may be combined with a compass associated with the athlete to increase accuracy of direction calculations.

FIG. 1 illustrates devices for monitoring of a physical activity in which a user 105 is involved. User 105 can be any person who is engaged in a physical activity such as a sport, exercise, physical training, and/or involvement in a physical activity for medical purposes such as rehabilitation from an injury or exercise to improve a medical condition. In addition, the physical activity could be a work activity that involves physical movement and/or mental stress, such as a firefighter.

Mobile device 110 is used to monitor various characteristics or metrics associated with the physical activity. Mobile device 110 may be a cellular phone, a smartphone, a tablet computer, a notebook computer, a multimedia player, an audio player, a personal digital assistant (PDA), a GPS receiver, or a combination thereof. It should be understood that the techniques introduced herein are not to be limited to any particular type of mobile device or hardware platform. In some situations, mobile device 110 may include wireless communication capabilities enabling it to transmit and/or receive data without necessarily having a physical or hard-wired connection to the device(s) it is communicating with. Mobile device 110 may be semi-permanently attached to user 105 using a strap, an armband, a holster, a clip, a strap, a tether, a belt, or semi-permanently attached to user 105 using a piece of clothing or gear with a pocket or compartment for mobile device 110. While mobile device 110 may be attached to or carried by user 105 in some cases, mobile device may only be in proximity to user 105 in other cases (e.g., attached to a piece of equipment that is near user 105).

Mobile device 110 includes sensor 115. Sensor 115 may be any of the one or more types of sensors described herein for measuring data related to a physical activity of user 105, a piece of equipment associated with the physical activity, and/or other data related to the physical activity (e.g., an environmental condition). Sensor 115 may be a sensor that is inherent to mobile device 110 and is configured to server other purposes in mobile device 110. For example, sensor 115 may be a gyroscope that was included in mobile device 110 for purposes such as navigation but may also be used for monitoring a physical activity such as measuring the movement of an arm or a leg. Alternatively, sensor 115 may be a sensor that is included in mobile device 110 but is not used by mobile device 110 for purposes other than for monitoring of physical activities as described herein. For example, sensor 115 may be a sensor associated with measuring of oxygen saturation that would not serve other purposes with respect to mobile device 110. The terms "sensor" and "data collector" are used interchangeably herein.

Mobile device 110 may be placed or held in a position that is selected for purposes of measuring a particular physical or physiological data related to user 105. For example, mobile device 110 may be attached to a wrist of user 105 for purposes of measuring arm movement. In another example, mobile device 110 may be placed close to a major artery such that sensor 115 can measure blood flow in that artery. In some situations, mobile device 110 may be a custom configured or specialized model of a general purpose mobile device that includes sensor 115, or other devices and/or software, for the purposes of measuring or monitoring data related to an activity. Sensor 115 is described as a single sensor, but could also be a plurality of sensors, including a variety of types of sensors. Sensor 115 may also be a sensor having multiple components.

Sensor 120 is a sensor that is external to mobile device 110. Like sensor 115, sensor 120 may be any of the one or more types of data collectors or sensors described herein for measuring physical or physiological data related to a physical activity performed by user 105, measuring other data related to a piece of equipment associated with the physical activity, and/or other data related to the physical activity. Sensor 120 may be used in a manner similar to that described above with respect to sensor 115. Sensor 120 may be attached to mobile device 110, to user 105, or to both. In some cases, sensor 115 and sensor 120 may be used together. For example, sensor 120 may be a sensor for converting a physically measured parameter into a signal, a voltage for example, and sensor 115 may receive and convert that voltage into information used by mobile device 110 to determine the characteristic. In other cases, data obtained from sensor 115 may be combined with data from sensor 120 to determine a characteristic.

Sensor 120 may communicate with mobile device 110 using wired, wireless, and/or optical communication techniques. Sensor 120 and sensor 115 are described as a single sensor, but could also be a plurality of sensors, including a variety of types of sensors. Sensor 120 may be placed in a variety of locations on or near user 105. In some cases, sensor 120 may be included in an item worn by user 105 such as a piece of clothing, a hat, shoes, a bracelet, a wristband, glasses, an earpiece, an earbud, a chest strap, a ring, a scarf, a watch, an armband, and/or a glove.

Data from multiple sensors, such as sensor 115 and sensor 120, may be used to compute a single characteristic or metric. Alternately, data from a single sensor may be used to compute multiple characteristics or metrics. In some cases, multiple metrics may be used to compute a more general, or broader, performance metric that is representative of the various information used to compute it. For example, various metrics such as heart rate, breathing rate, and energy expended during an exercise routine may be combined to arrive at a more generalized fitness level metric. Many other combinations are possible.

A characteristic or metric determined using the techniques described herein may be displayed to user 105, may be stored in mobile device 110, and/or may be transmitted to one or more other devices. The metric may be displayed using a display of mobile device 110, such as a liquid crystal display (LCD) screen of mobile device 110. The resulting metric may also be presented to user 105 in other manners such as, for example, using audio, through a heads-up display, or through a haptic feedback mechanism.

The amplitude, timing, and duration of the haptic signal can be varied to indicate to a user the nature of the notification. The haptic signals can include vibrations and other types of mechanical motion felt by a user as well as direct electric discharge. In some cases, the haptic feedback may be delivered in the form of tightening and/or loosening of an arm strap. Direct electric discharge can be a low current discharge that is detected on the skin, or a higher discharge that causes physical discomfort. Haptic actuators can include, but are not limited to, vibrating motors, electrically conductive surfaces coupled with a charge creator, subsonic sound waves, electroactive polymers, piezoelectric actuators, electrovibration actuators (e.g., indirect charge actuators such as TeslaTouch®) and the like. Electroactive polymers (EAPs) may be used to cause deformities in a surface (e.g., protrusions or depressions) following application of a voltage difference across the electroactive polymer. The electroactive polymers may be: dielectric EAPs, such as ferroelectric EAPs (e.g., polyvinylidene fluoride); electrostrictive graft polymers; or liquid crystal polymers. The EAPs can also be ionic EAPs, such as an electrorheologic fluid or an ionic polymer-metal composite. An ionic EAP may be coated with a waterproof polymer that can deform along with the ionic EAP to produce a deformity that can be detected by touch or even sight.

A metric may be displayed in a variety of ways including quantitatively, qualitatively, comparatively, in the form of a chart, in the form of a table, and/or in the form of a graph. The metric may be displayed in many different formats including: relative to a typical or average performance of user 105 (e.g., user averages 7.3 mph in previous runs and is averaging 7.5 mph this time), relative to a performance of a professional athlete (e.g., user is riding 77% as fast as professional Joe Smith), relative to a performance of group of professional athletes (e.g., user is riding 68% as fast as last year's Tour de France finishers), relative to user 105's competitors in an event (e.g., heart rate is 92% of the average heart rate of all of the other competitors in the event), relative to a circuit or course the activity is taking place on (e.g., watts of power generated per lap of the course), relative to a particular location on the course (e.g., blood glucose level is lower than expected for the last stage of a triathlon), relative to a personal best of user 105 (e.g., 28 seconds off of his or her best time for this course), relative to a personal worst of user 105, relative to a goal of user 105 (e.g., swinging a golf club 5 mph slower than a target of 85 mph), or relative to a limit or threshold (heart rate has exceeded preferred maximum heart rate by 4 beats per minute). One or more metrics may also be displayed graphically with respect to time to indicate progress with respect to training, with respect to medical treatment, with respect to changes in equipment, with respect to changes in diet, and/or with respect to peers.

The data gathering, communication, and display techniques described herein may be implemented with the aid of a software application (an "app") or software program executed by one or more computer processors of mobile device 110. The app may display the gathered data, communicate the gathered data, and/or store the data. The app may also process the gathered data. Furthermore, the app may also permit user 105 to configure the app, configure a sensor, calibrate a sensor, select display options, set thresholds or limits, and/or set data sharing options. The app may also let a user enter goals, thresholds, or limits with the app warning or alerting the user when one of the goals, thresholds, or limits has been met or exceeded. In some cases, one or more software applications that perform some or all of these functions to determine a set of characteristics may be referred to as characteristic generation programs.

Bicycling sports, such as road bike or mountain bike racing can have a variety of data sources in addition to physiologic characteristics detected by sensors on or near the body of the athlete. For example, pedal data such as pedal cadence or pedal force exerted by the athlete may be acquired using status monitoring sensors. Data from sensors attached to the wheels or frame of the bike may also be utilized, including data related to the number of wheel rotations and wheel rotation rate. Distance traveled can also be calculated if the circumference of the wheel is known. Both pedal and wheel data can be acquired using a Hall effect sensor or a reed switch, in which a magnet is attached to the wheel, crankshaft, or pedal and activates the Hall effect sensor or reed switch (attached to a portion of the frame) to allow detection. Alternatively, the magnet may be fixed to the frame and the sensor may be attached to the wheel or pedal assembly. A sensor may also be used to detect the gear being used by the bicyclist (see, e.g., U.S. Pat. No. 6,569,045, incorporated herein by reference in its entirety). Torque sensors installed in the bottom bracket or crankshaft assembly of a bicycle may be used to detect the torque applied by the athlete to the crankshaft. Exemplary torque sensors may include strain gauges and surface acoustic wave sensors.

Torque sensors may also be attached to athletic equipment that is used in other sports. Exemplary sports equipment include, without limitation, racquets (e.g., tennis, racquetball, squash, etc.), bats or clubs (e.g., golf, baseball, cricket, etc.), paddles (e.g., kayaking, canoeing, etc.), masts (e.g., sailboats, sailboards, etc.), wheels (e.g., skateboarding, snowboarding, etc.), skates (e.g., iceskating, speedskating, etc.). Data from these sensors may be used to determine the amount of force or torque being applied to or being experienced by the piece of sporting equipment.

The speed of a bicyclist can be inferred from pedal and/or wheel data, as well as using GNSS receiver data. The number of laps completed around a course can also be inferred from wheel data, GNSS receiver data, as well as data from fixed relays placed on a course or track that can be used to determine location. Side-to-side sway of the bicyclist while pedaling can also be measured using accelerometers or gyroscopes, and correlated with or interpreted with other data, such as crankshaft torque.

Data from swimmers may also be collected. Data concerning the stroke and kick may be collected using sensors on the hands, arms, legs, and/or feet that can detect aspects of the stroke and kick. For example, accelerometers or gyroscopes coupled to low power transmitters may be placed on straps or directly adhered to one or both of a swimmer's legs to detect each kick. Optical transceivers that send one or more wavelengths of light and detect their reflectance from the other leg may also be used. The sensors may be or may include radio frequency identification (RFID) tags, either powered or unpowered, that can communicate with a powered transceiver on the other leg that can detect the changes in proximity between the legs for every kick and relay that information to a controlling device, such as a mobile electronic device, a mobile phone, or a smartphone.

Similarly, accelerometers, gyroscopes, optical transceivers, and wireless radio transmitters, such as RFID tags, may be used to detect stroke completion. The sensors may be on one or both arms. The controlling device may be attached to the swimmer by a strap or shirt and located on the torso, waist, arm, or leg. If the controlling device is attached to the torso or waist of the athlete, the controlling device can act as a transceiver for RFID tags and detect the proximity of an RFID tag on the forearm or wrist. Combinations of different sensors may also be used, such as an accelerometer and an RFID tag on the swimmer's wrist. Analysis of the combined data can be used to determine the shape of the swimmer's stroke during the pull phase. Accelerometer or gyroscopic sensors on the head may be used to determine head angle and head turning to detect breaths taken, as well as flip turns.

Real-time distance to an object, such as buoy or wall, may be determined using a GNSS transceiver or receiver on a controlling device or using a separate sensor that communicates with the controlling device. The distance can also be estimated from stroke and/or kick data. In some embodiments, fixed RF relays associated with the wall or buoy may interact with a location sensor or controlling device on the athlete and communicate the distance in real-time as the athlete approaches the object. For example, the controlling device may provide an audio signal to waterproof earphones related to the distance, such as a countdown of distance or a series of repeated short noises that increases (or decreases) in frequency as the athlete approaches the object. In some embodiments, the athlete is signaled by a repeating haptic or electrical pulse that increases (or decreases) in frequency as the athlete approaches the object.

In one embodiment, a controlling device, such as a mobile computing device, may include a camera that can detect a lane line in the bottom of a pool. The controlling device is strapped to the torso, waist, or leg of the swimmer with the camera pointed at the bottom of the pool that has a lane line with at least one distinguishing feature (e.g., individual markers or tiles along its length, markers or tiles one at least one end of the lane line, a change in shape, color, or contrast at an end of the lane line). As the swimmer moves along the lane line, the camera detects the distinguishing features and calculates an instantaneous and/or average velocity.

In some embodiments, the controlling device may also calculate the distance traveled by the swimmer. The markers or tiles may have a pattern or color that can easily be distinguished to determine a location within the pool. The markers may also have lights (e.g., LED or laser lights) that emit wavelengths of light that can be detected by the camera of the controlling device. Alternatively, the controlling device may include a specialized light or RF sensor component that communicates in a wired or wireless manner. In some embodiments, the markers make up the lane line itself (e.g., the lane line is made of tiles surrounded by a different color border). The lane line may be painted on a rough surface that has irregular dark and light areas that are distinguished by the camera. In some embodiments, the markers are removably placed in an existing lane or along a lane divider.

In some embodiments, individual removable markers may be placed on the bottom of a pond, lake, sea, ocean, or other body of water that is shallow enough to allow the camera to detect the markers (e.g., for use in triathlons or other outdoor swimming events). In some embodiments, the markers include an RF transmitter or transceiver that communicates with a controlling device and allows use in turbid water. In some embodiments, the markers include a tethered flag that is held in negative buoyancy relative to the marker; such a tethered flag allows the markers to be visually located by a person and removed from the body of water after the race has been completed.

Markers with RF transmitters and/or light transmitters may also be attached to buoys at or near the surface of the water, or may be associated with a buoyant material, a weight, and a tether to allow the marker to act as a buoy itself. Markers may be used for other watersports that may utilize a slalom course, including waterskiing, wakeboarding, kneeboarding, windsurfing, kiteboarding, personal watercrafting (e.g., "jet skiing"), surf skiing, stand up paddleboarding, kayaking, canoeing and the like.

In the various examples described herein, the measured and/or collected data that is not physiological data may be referred to as physical data.

Figure 2:
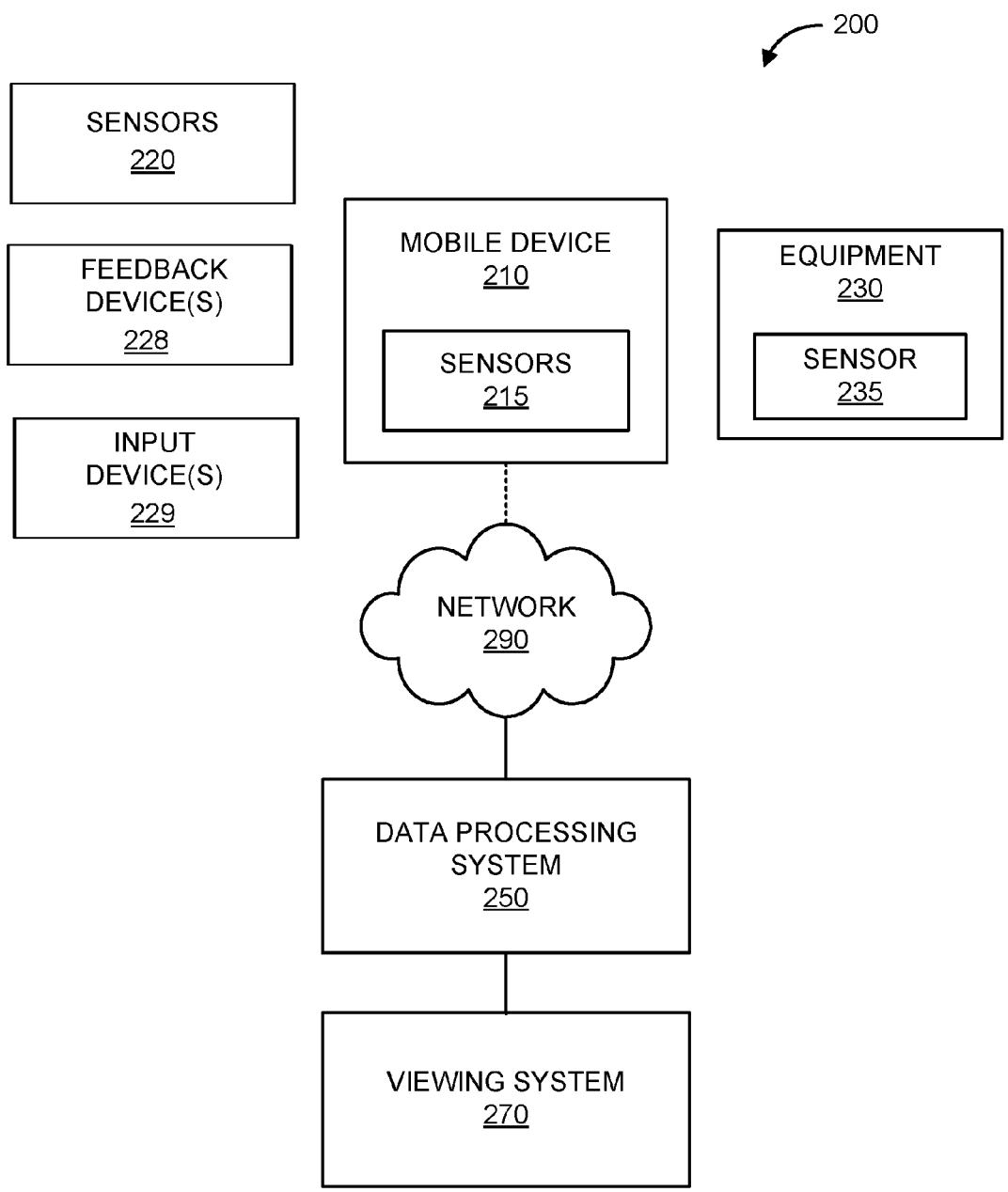
FIG. 2 illustrates a system for determining characteristics of a physical activity.

FIG. 2 illustrates system 200 for monitoring a physical activity. System 200 includes mobile device 210, sensors 220, feedback device(s) 228, input device(s) 229, equipment 230, data processing system 250, and viewing system 270. Mobile device 210 is an example of mobile device 110. Mobile device 210 includes sensors 215. Sensors 215 and sensors 220 are examples of sensor 120 and may be attached to, or otherwise associated with, a participant in a physical activity who is using mobile device 210.

Equipment 230 is any type of apparatus, clothing, device, or implement that is used in conjunction with performing a physical activity. Some examples of equipment 230 are a bicycle, a javelin, a discus, a surfboard, a baseball bat, a piece of clothing, a piece of protective equipment, a golf club, a breathing apparatus, a tool, a ski, and/or a ball. Many other types of equipment are possible. Equipment 230 includes sensor 235. Sensor 235 is any type of data collecting device used to measure a state, condition, or use of equipment 230. For example, sensor 235 may include a strain gauge, an accelerometer, a gyroscope, a load cell, a temperature sensor, a pressure sensor, and/or a sensor for measuring some other state, condition, or use of equipment 230. In one example, equipment 230 is a baseball bat and sensor 235 measures the acceleration and speed of the bat when it is swung. In another example, equipment 230 is a firefighter's helmet and sensor 235 measures one or more conditions of the air near the helmet.

Network 290 may be any type of computer network for communicating data. Network 290 may be a Local Area Network (LAN), a Wide Area Network (WAN), the Internet, a wireless network, a private network, a dedicated network, a Wireless Fidelity (WiFi) network, or a combination thereof. Network 290 is used to communicate data between mobile device 210 and data processing system 250. In some situations mobile device 210 may communicate to network 290 through a wireless connection.

Data processing system 250 is any computing device or group of computing devices configured for storing and/or processing data provided by mobile device 210. Data processing system 250 may be a computer, a group of computers, a distributed computer, a server, and/or a group of servers. Data processing system 250 may also include or provide access to a data storage system. The devices which make up data processing system 250 may be dedicated to the processes described herein or may be shared with other computing functions. If data processing system 250 is made up of several devices, the devices may be in a same location or may be distributed across multiple geographic locations.

Similar to the process described with respect to FIG. 1, sensors 215, sensors 220, and/or sensors 235 are used to obtain data relating to a physical activity performed by a user of mobile device 210. After receiving data from the various sensors, mobile device 210 may process the data and display the data to the user as described with respect to FIG. 1. Alternatively, or in addition, mobile device 210 may transmit some or all of the data to data processing system 250. Data processing system 250 may receive data from a plurality of users. In other words, data processing system 250 may be a processing hub for multiple athletes or competitors. In some situations, the plurality of users may be participating in or competing against each other in a sporting event. For example, data processing system 250 may be receiving data from multiple players of a team playing in a hockey game and may be receiving data from one or more players of the opposing team at the same time. In another example, a doctor or medical researcher may gather data from multiple patients or subjects using data processing system 250.

A protective case may be applied to mobile device 210. The protective case may protect mobile device 210 with respect to dust, dirt, water, snow, abrasion, impact, shock, crushing, and/or other damaging elements or forces. The protective case may also perform other functions in addition to providing the physical protection to mobile device 210. For example, one or more of sensors 215 or sensor 220 may be included in the protective case. In addition, some or all of the processing of the data from one or more of sensors 215, 220, and/or 235 may be performed by the protective case. In other words, in addition to providing physical protection to mobile device 210, the protective case may also provide signal sensing, signal detection, signal conditioning, communication, data storage, computer processing, and/or data processing capabilities.

Sensors 220 and/or sensors 235 may communicate with mobile device 210 using a variety of communication formats and/or protocols. The communication may be conducted using Bluetooth, Bluetooth Low Energy, WiFi, near field communication (NFC), optical communication, IR communication, or a combination thereof. The type of communication used may vary depending on the type of sensor, where the sensor will be placed, how far the sensor will typically be located away from mobile device 210, the operating environment, and/or power issues.

Data processing system 250 processes the data using any of a wide range of data processing algorithms and statistical methods in order to indicate the participants' physical conditions and performance, compare the participants' physical conditions and performance, and/or project the participants' expected future performance. The processing may be performed by data processing system 250 using raw data captured by mobile device 210 from the sensors or may be performed based on data received by data processing system 250 that has already been partially processed by mobile device 210. Various pieces of measured data may be combined to generate a more general performance metric or indicator rather than having a larger number of individual metrics. In one example, an oxygen saturation measurement and a breathing rate measurement may be combined according to a formula or algorithm to arrive at a broader metric that may be called a "breathing index." It should be understood that many other combinations of metrics and characteristics are possible. In some situations, multiple metrics and/or characteristics may be aggregated to generate a profile for the participant.

In some situations, calculation of a metric may involve use of another metric that was captured at a different point in time. For example, it may be desirable to generate a metabolic equivalent (MET) measurement for a physical activity. MET is calculated as a reference to resting metabolic rate (RMR). Rather than using a standard reference value for RMR, system 200 may be used to perform measurements and make a determination of an actual value for the RMR that is later used as a reference for calculation of a MET for that individual.

The sets of characteristics and/or other information generated by data processing system 250 may be quantitative, qualitative, and/or may be presented in graphical form. The information may be presented in the form of a line chart, a bar chart, a trend chart, a scattergram, or another type of graphical display format. In some cases, changes in the characteristics may be displayed with respect to the passage of time. Historical information regarding the characteristics may be retrieved from a database or other storage location in order to generate a representation of how one or more characteristics have changed over time.

In some situations, data processing system 250 transmits the some or all of the processed data back to mobile device 210. The data transmitted to mobile device 210 may also include data associated with participants other than the recipient. For example, in addition to seeing a display of his or her own physical conditions and performance, the user of mobile device 210 may see similar statistics for one or more of his teammates and/or one or more of his or her competitors. The information may also include indications of past performance levels, maximums, thresholds, or other historical data related to one or more of the participants thereby enabling participants, fans, teammates, coaches, managers, trainers, persons betting on the event, persons have another type of financial interest in the event, or other interested individuals to estimate how much reserve energy or strength a participant may or may not have.

Data processing system 250 may also transmit data to viewing system 270 in addition to, or in place of, transmitting data to one or more mobile devices. Viewing system 270 may be a video monitor, a scoreboard, a website, a database, an email server, a text server, a projection system, and/or an electronic information dissemination system. Viewing system 270 may be part of or may provide information to a coach, virtual coach, a betting system, or a handicapping system, and may provide warnings or alerts when one or more of a participant's metrics deviate from a preferred range.

In one configuration, viewing system 270 may provide information to spectators regarding multiple competitors who are competing in a professional sporting event. In this example, viewing system 270 may provide information regarding measured physical characteristics or metrics of multiple players as measured by sensors such as sensors 215, 220, and/or 235 that are associated with each of the players. In one example, the average heart rate, maximum heart rate, oxygen saturation, and lactic acid levels of multiple swimmers in a competitive race may be displayed for viewing by spectators, coaches, and/or bettors. In another example, the participants are golfers and, in addition to data gathered from their bodies using sensors 215 and 220, sensor 235 gathers information about their swings from their golf clubs.

In some situations, data processing system 250 may also transmit information about the field of competitors back to the mobile devices of the competitors. In other words, an athlete may use mobile device 210 to capture, transmit, and view his or her own metrics while also using it to view some or all of the metrics of his or her competitors. The previously discussed software app may be used to manage which information is displayed and the format of that display. Different sets, or subsets, of the gathered information may be shared with different parties. For example, the most detailed, accurate, or extensive information associated with a particular user may be made available to that user and/or his or her coaches. Less detailed, less accurate, less extensive, and/or less timely information may be made available to spectators or viewers of the event. Similarly, only subsets of a participant's information may be provided to his or her competition.

Data processing system 250 may also receive or retrieve data from other sources. For example, while data processing system 250 is receiving data regarding current performance of an event participant, it may also retrieve historical data related to that participant from a data storage location, from a computer system, or from a web page. Data processing system 250 may utilize network 290, or another network, to receive or retrieve this other data. The historical data may be used for purposes of comparison with current or more recent data.

System 200 may perform steps to improve the accuracy of the data captured by mobile device 210 and the associated sensors. In some situations, it may be possible to determine a particular metric from more than one sensor or data source. For example, it may be possible to independently estimate heart rate based on an electrical sensor attached to the chest, based on an optical sensor inserted in the ear, and through monitoring of brain functions. Mobile device 210 and/or data processing system 250 may use one or more of a variety of algorithms to determine the most accurate value for heart rate. Algorithms may include averaging results from all of the sensors, averaging results from a subset of the sensors, weighting the results provided by each of the sensors, and/or using other statistical methods for arriving at a more accurate value for a metric based on data received from two or more sensors, including different types of sensors or sensors using different measurement techniques.

Selecting which data to rely on in determining a particular metric or determining how to weight the data from a variety of sensors may also include other types of determinations or assessments. For example, the other determinations or assessments may include determining which type of sensor should be capable of providing the most accurate reading, assessing a sensor's current state, assessing a sensor's recent performance, assessing a sensor's results compared to other sensors, assessing a sensor output compared to an expected value, and/or analyzing previously generated calibration information for the sensor.

The processes and techniques provided herein for computing more accurate metrics based on input from multiple sensors or devices may also include applying correction values or mathematical functions to the data received from one or more of the sensors. The correction value or function may be generated as a result of a calibration activity. In some cases, the calibration activity may be performed periodically in order to properly adjust for changing conditions or sensor characteristics.

In some situations, a metric may be made more accurate by obtaining data from another source or sensor. In one example, sailors racing in a boating event may use sensors to measure environmental variables such as temperature, wind speed, barometric pressure, and location. Based on the location information, a central processing system can determine which sailors are close to each other. If sailors that are close to each other are reporting significantly different environmental metrics, the system may determine which of the readings is/are more accurate using one of the techniques described herein and generate a more accurate value. In another example, it may be possible to determine a cyclist's location on a course using a variety of methods that may utilize inputs from a compass, a GPS receiver, a gyroscope, and/or an accelerometer. The data processing system may evaluate the inputs from these different sources to combine or eliminate some of them in order to make the most accurate location determination. In some cases, the system may transmit the information that is determined to be more accurate back to one or more participants.

A person using mobile device 210 may also share some or all of the gathered physical activity data or metrics through social media. For example, after completing a swim, some of the data gathered during the swim may be transmitted from mobile device 210 to Facebook®, to Twitter®, in an email, in a text, as a blog post, and/or to a website. The data may be transmitted as a Facebook® post with information about the distance swum, time required, calories burned, water temperature, and/or time of day. Information may also be included to support generation of a map of the area or route swum. In addition, one or more pictures associated with the swim may be transmitted to Facebook® in conjunction with the post. A software application running on mobile device 210 may assist the user in selecting which data will be transmitted, how it will be formatted, selection of pictures, and/or other formatting or configuration choices. A website or social media page may be allow various people participating in similar activities to post, share, or compare data. A software application running on mobile device 210 may be configured to interface with the website or social media page. Using these methods, various parties may easily compare metrics and performance characteristics to each other even though they may not be in the same geographic area.

Although the communication between mobile device 210 and data processing system 250 is illustrated in FIG. 2 as occurring through network 290, other configurations are possible. In one example, mobile device 210 may communicate directly with data processing system 250 without the use of a network. In another example, communication between mobile device 210 and data processing system 250 may be conducted through multiple networks. In some configurations, mobile device 210 may transmit gathered and/or processed data to multiple systems, such as data processing system 250.

In addition to displaying information to a user regarding his or her own performance characteristics, mobile device 210 and/or an app running on mobile device 210 may provide feedback to the user in other forms using one or more feedback devices such as feedback device(s) 228. In one example, mobile device 210 may provide a metronome function. This may be helpful for a user who is trying to maintain a particular pace or cadence, such as a runner or bicyclist. The metronome information may be communicated to the user audibly, visibly, haptically, and/or through one or more of sensors 220 or sensor 235.

Mobile device 210 and/or an app may also provide other types of information or feedback to update a user regarding measured physiological parameters, measured environmental parameters, exercise targets, and/or exercise progress. One example includes providing audible signals or visual indicators to the user indicating whether the user needs to exercise more quickly or more slowly to achieve or maintain a specified target. Another example includes transmitting audible signals to an emergency first responder and/or a manager of an emergency first responder indicating whether the first responder has exceeded or is close to exceeding a specified physiological parameter such as heart rate or body temperature.

In further examples, environmental parameters may also be used in determining or adjusting a physiological or exercise target for a user. For example, a user's target heart rate or permitted heart threshold may be adjusted based on factors such as: ambient temperature, ambient humidity, air quality, elevation, and/or other environmental variables. One or more of these variables may be determined by mobile device 210 such as determining elevation using a GPS receiver.

In another example, mobile device 210 may electromyographically stimulate the user's muscles to assist the user in keeping a pace, to assist the user in using the muscles more effectively, or to help the user with the timing of use of the muscles. Electromyographic stimulation may be used as part of a training regimen, as part of rehabilitation, for physical therapy, and/or for medical treatment. Different muscle stimulation programs or profiles may be loaded in or configured on mobile device 210 for use by an athlete.

Electromyographic methods may be used at various strength levels. For example, a light stimulation may be used to remind an athlete to stay on a particular pace by encouraging him or her to use a particular muscle or perform a particular motion on a particular pace. In another example, a stronger stimulation may be used to more aggressively trigger user of a particular muscle at a particular time. This may be useful for strength training or in rehabilitation applications where a user may not currently have good control over his or her muscles.

The data gathered by mobile device 210 may also be used to provide feedback or information back to the user in other ways. In one example, the rate of a pacemaker may be proactively or preemptively adjusted based on a level of exercise or other physical conditions detected using one or more of the sensors. In another example, the dosage of a drug that is automatically released or administered may be adjusted based on information obtained from one or more of the sensors. In one configuration, the sensor is measuring data directly related to a medication and the measurement indicates more or less of the drug is required. In another configuration, the sensors are measuring general physical activity parameters and a relationship between the dosage required and the physical activity level are understood such that the dosage can be preemptively adjusted based on a changed activity level rather than waiting for the person's physiological reaction to the changed activity level and the direct sensing that a change in dosage is needed.

A doctor may use some or all parts of system 200 for evaluating a patient or evaluating an injury of a patient. In some situations, a patient may provide data obtained by system 200 to a doctor or provide the doctor access to the data within system 200 that was previously captured. In some situations, en employer or military entity may use a system such as system 200 to gather information about people who perform tasks requiring physical activity and may evaluate employees or plan work assignments based, at least in part, on this information. For example, soldiers may be selected for various challenging and/or stressful duties based on information related to physical and/or mental performance using a system such as system 200.

In some configurations, mobile device 210 and/or data processing system 250 may transmit data gathered about a user's condition directly to a doctor or other treatment provider. The doctor or treatment provider may also be able to transmit information to mobile device 210 regarding a change in treatment. The change in treatment may be a change in an exercise routine or regimen that is transmitted to mobile device 210 for use by the patient or may be an adjustment to a piece of medical equipment used by the patient. For example, equipment 230 may be a rehabilitation apparatus used by a patient. Based on information obtained using the techniques described herein, the treatment provider may adjust the treatment and remotely or electronically adjust equipment 230 to implement these changes. In some cases, a warning or alert may be generated when a parameter exceeds a threshold recommended or set by a medical provider. The warning or alert may be displayed to the user on mobile device 210 and/or may be transmitted back to the medical provider.

In changing a dosage or treatment for a patient, various levels of security or approvals may be required. For example, in adjusting a medicine dosage or treatment profile remotely, a treatment provider may be required to successfully navigate one or more security requirements to verify his or her identity and authority to make the changes. In addition, the user or patient may also be required to approve any changes or updates provided by a third party before they are implemented. System 200 may enable the doctor or treatment provider to monitor the patient on a real-time or near real-time basis. This may be particularly useful when the patient is experiencing unusual conditions, as indicated by data captured from the sensors, or during a period after a treatment or medicine dosage has been adjusted.

In some situations, mobile device 210 may be attached to a user or may be held in place on the user using a flexible strap or band. Mobile device 210 may also be secured or held in place on the user through use of a case, a holster, a fixture, or a rigid mounting portion configured to receive mobile device 210 and hold mobile device 210 in place on the user. In some implementations, mobile device 210 may be held in place using a flexible strap and a rigid mounting portion. The term "arm strap" is used herein to describe any type of device that may include a strap and/or a rigid mounting portion for holding mobile device 210 in place. While the term "arm strap" is used, a similar band or strap may also be used on another part of the body such as the wrist, leg, arm, ankle, head, temple, waist, back, or chest. Rather than being elastic in nature, the arm strap may also be adjustable and held in place using a fastener such as Velcro®.

In some implementations, sensors 220 may be mounted in, attached to, or held in place by an arm strap. In other words, the arm strap may serve a dual function of retaining sensors 220 and mobile device 210. In other implementations, sensors 220 may be attached to or held against the body of the user in one location while mobile device 210 is secured to the user in another location on the body.

The arm strap may also include or provide one or more other functions to mobile device 210 and/or sensors 220. The arm strap may include one or more additional functions for controlling or interfacing with mobile device 210, sensors 215, and/or sensors 220. For example, the arm strap may include one or more buttons or input devices, such as input device(s) 229, for controlling or providing an input to mobile device 210. The one or more buttons or input devices may be tactile buttons for providing audio control inputs to mobile device 210 such as volume control, mute, and or track control. The tactile buttons may be easier for a user to reach, access, or find when mobile device 210 is attached to his or her body. The buttons may be located or accessed more easily than the user would be able to access these controls directly on mobile device 210, particularly in the case where mobile device 210 is a touchscreen device because the user may not have a direct view of the touchscreen and/or may have to enter a passcode to access the device. This can be particularly helpful when the user is attempting to access these types of controls while involved in a physical activity such as running, swimming, or biking.

One or more buttons on the arm strap may also be used for input associated with an exercise or data gathering function. In one example, a button may be used to trigger a visual or audio update regarding the exercise activity. Pressing a button on the arm strap may trigger the software application to generate an audio message transmitted to a speaker of mobile device 210 or through headphones attached to mobile device 210.

A software application running on mobile device 210 may also be used to program features or characteristic of the buttons or control features on the arm strap. The function(s) of the buttons or control features may be changed or programmed by a user.

Using the techniques described above, the user can interact with frequently accessed features, such as audio controls, via the arm strap without directly interacting with mobile device 210. The arm strap may communicate these inputs or interactions to mobile device 210 using a wired or a wireless connection. A wireless communication link may permit these types of interactions between the arm strap and mobile device 210 to be performed even when mobile device is not attached to or seated in the arm strap, such as, for example, when a user is running on a treadmill and has mobile device 210 lying on a console of the treadmill.

In another example of arm strap functionality, the arm strap may include one or more visual indicators or display elements. The arm strap may include an indicator that display status associated with mobile device 210 and/or sensors 220. For example, the arm strap may include an LED that flashes when a new email, voice, or text message is received by mobile device 210. This may be beneficial if related indicators on mobile device 210 are not facing the user and the visual indicators or display elements on the arm strap are positioned such that the user can more readily see them. This type of information may be communicated between the arm strap and mobile device 210 using a wired connection or using a wireless connection.

In further implementations, sensors or information available in mobile device 210 may be used to improve measurements made using sensors 220. For example, in cool weather it may be desirable to wear a module containing sensors 220 on a wrist, hand, ankle or some other area of the body where it is easier to attach or access while wearing long sleeves or other cool weather gear. These areas may be more accessible for the user but may cause additional challenges with respect to obtaining accurate readings from sensors 220. These additional challenges may be due to sensors 220 and/or the measurements of sensors 220 being subject to increased motion artifacts (i.e., the additional movement at a runner's wrist relative to the motion that occurs at the upper arm, chest, waist, or head). These additional challenges may also be due to sensors 220 being placed on a portion of the body that is not as well suited for making the measurement (i.e., it may be more difficult to detect blood flow or heart rate on the wrist than it is to do so on the upper arm).

In order to address the problems discussed above, information form mobile device 210 and/or sensors 215 may be used to supplement, adjust, correct, filter, correlate, normalize, or otherwise process data received from sensors 220. In one example, sensors 220 are subjected to the additional motion and motion artifacts associated with being placed on a runner's wrist. In addition to sensors associated with measuring heart rate, blood flow, and/or other physiological parameters, sensors 220 may also include an accelerometer, gyroscope, GPS, and/or magnetometer for measuring motion, position, or location of the user. While information from these sensors may be used to attempt to factor out, subtract, or filter motion artifacts present in the physiological measurements, doing so may be difficult due to the additional motion associated with the sensors having been placed on the wrist or ankle rather than on a more stable portion of the body such as the arm or waist.

In situations like those described above, data obtained from an accelerometer, gyroscope, GPS, and/or magnetometer of mobile device 210 may also be used in attempting to factor out, subtract, or filter the increased motion artifacts present in the physiological measurements. Motion data from mobile device 210 may be used in various ways with respect to the motion information from sensors 220. The data from mobile device 210 may be used in place of the data from sensors 220. The data from mobile device 210 may also be used to supplement the data from sensors 220. The data from mobile device 210 may also be used to adjust, correct, filter, correlate, normalize, or otherwise process the data from sensors 220. The motion data from mobile device 210 may be used to better determine how the motion data from sensors 220 should be used to be remove motion artifacts from the measure physiological data. Many algorithms are possible and the techniques described herein are not to be limited to any particular algorithm.

In one implementation, an activity monitoring apparatus may be attached to the body of a person performing a physical activity. The activity monitoring apparatus includes a retention feature configured to removably secure the monitoring apparatus to the person. The activity monitoring apparatus also includes a clasping mechanism configured to receive a mobile electronic device and removably secure the mobile electronic device to the monitoring apparatus. In some cases, the mobile electronic device may be enclosed, at least partially, in a protective cover and the activity monitoring apparatus is configured to clasp or retain the protective cover.

The activity monitoring apparatus may include a physiological data collector and electronic circuitry. The physiological data collector is configured to collect physiological data associated with the person involved in the physical activity. Electronic circuitry is configured to receive the physiological data associated with the participant from the physiological data collector, process the physiological data, and wirelessly transmit the processed physiological data to the mobile electronic device for display on the mobile electronic device.

A single activity monitoring apparatus of the type described herein may be used on various parts of the body. In order to accommodate these various locations, the activity monitoring apparatus may have various features and/or interface to different attachments permitting it to physically interface with different parts of the body. In other words, various adapters may permit the activity monitoring apparatus to be attached to the arm, wrist, leg, ankle, waist, chest, or another part of the body. In some of these implementations, the activity monitoring apparatus may be configured to secure a mobile electronic device in the same location. In other implementations, the mobile electronic device may be secured or held in place in a separate location of the body.

In addition to monitoring and providing feedback with respect to athletic performance, the apparatuses, systems and methods described herein may also be used to protect a user from injury or danger. For example, the techniques described herein may be used by an emergency responder to monitor their physical condition in times of danger and stress. In addition, the techniques described herein may also be used to monitor and warn the user of dangerous environmental conditions the user may be exposed to such as temperature extremes and air quality issues. In some cases, monitoring of multiple members of a team may be performed by another, such as monitoring the conditions and environments of members of a fire crew fighting a fire.

Figure 3:
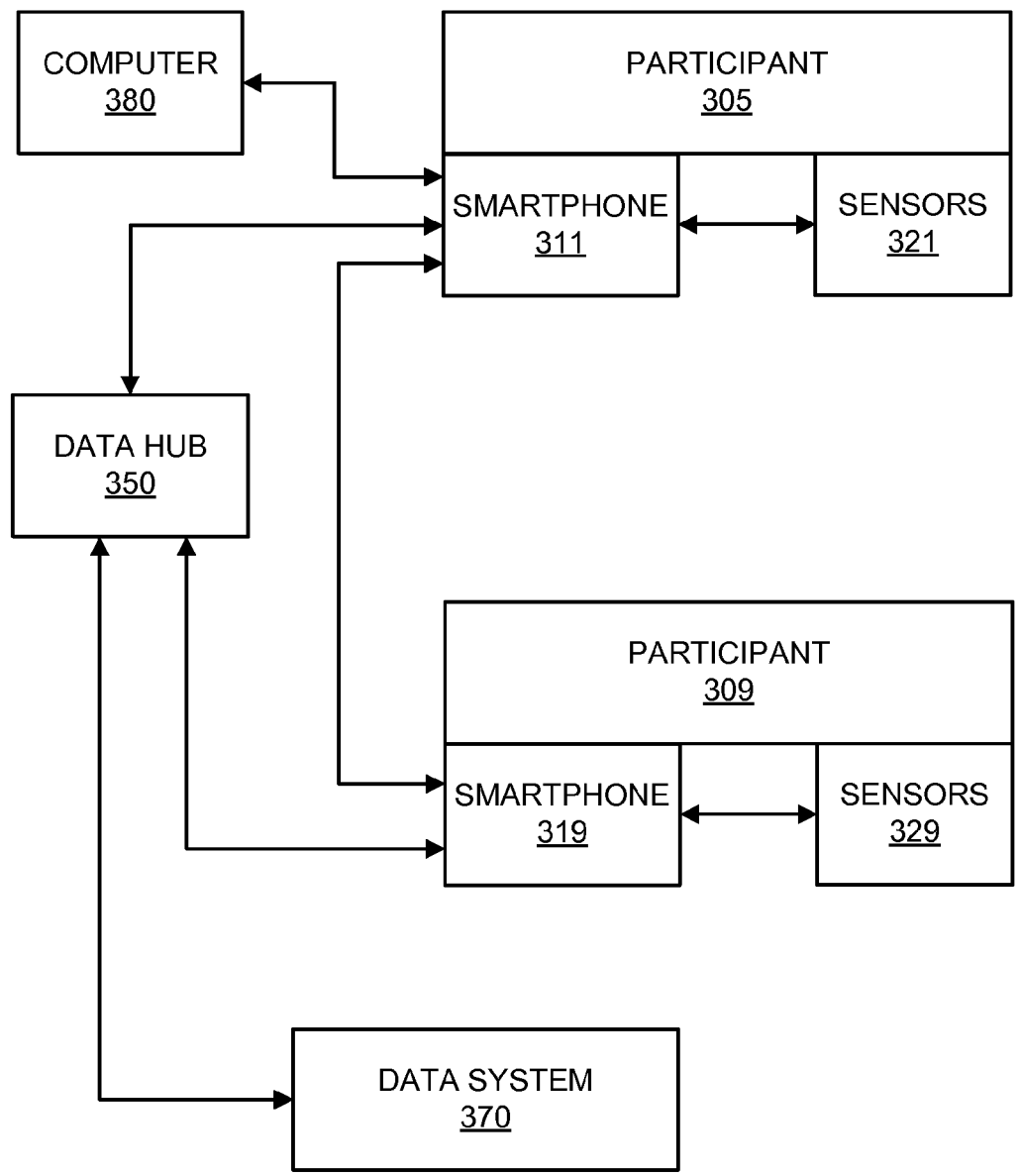
FIG. 3 illustrates determining characteristics of physical activities of participants in an event.

FIG. 3 illustrates determining characteristics of physical activities of two participants, participant 305 and participant 309, in a sporting event. The event could be a game, a sport, a competition, or a race. Each of the participants is using a smartphone, smartphone 311 and smartphone 319. Each of the smartphones is an example of mobile device 110 and/or mobile device 210. Each of the participants also has sensors, sensors 321 and sensors 329, attached to or in proximity to his or her body. The sensors are examples of sensor 120 and/or sensor 220.

Sensors 321 and sensors 329 are illustrated in FIG. 3 as being independent of other devices. However, in addition to or in place of these independent sensors, sensors could also be located in one of the smartphones, in a case for the smartphone, in a piece of clothing, in a piece of protective equipment, in an item worn by the participant, in a piece of sporting equipment, and/or in a device placed on or near a field or track associated with the event. Each of sensors 321 and 329 may be any of the types of sensors discussed herein. The sensors communicate with the associated smartphone over a data communication link or a data communication channel. The data communication link may comprise a wired connection, a wireless connection that uses radio frequency (RF) electromagnetic waves, an optical connection, or a combination thereof. The data communication link may also comprise connectors, ports, cables, interfaces, cables, fibers, or other devices associated with the communication link.

Participants 305 and 309 are competing against each other in a sporting event. There may be additional participants but only two participants are illustrated in FIG. 3 for purposes of clarity. The participants may be in the same physical location competing on the same field or course (e.g., mountain bike racing on the same course) or may be performing similar activities in two different physical locations (e.g., running on treadmills in two different geographic locations). As described in the other examples herein, the smartphones gather data associated with their respective participants using the sensors. The gathered data is related to one or more of: the performance of the participant, a physical condition of the participant, a physical condition related to a piece of equipment used in the activity, and/or a characteristic of the environment of the activity.

Some or all of the data captured by each smartphones is transferred to data hub 350 in real time, or near real time. Data hub 350 is an example of data processing system 250. Data hub 350 may be a single computing device or may be functionally distributed across multiple computing devices. In some configurations, data hub 350 may be implemented in one of the smartphones such that the consolidation of the data and other processing is performed in one of the smartphones. The data transmitted to data hub 350 from the smartphones may be transmitted in the form of raw data as it was collected from the sensors, may be partially processed by the smartphone before transmission, or may be fully processed by the smartphone before being transmitted to data hub 350. Processing the data my include applying one or more algorithms, filters, mathematical calculations, conversions, correlations, transformations, corrections, adjustments, and/or scaling factors to the data.

After the data from the participants has been accumulated and processed by data hub 350, it is transmitted for display, storage, and/or use. As illustrated in FIG. 3, data may be transmitted to data system 370, to one or more of the smartphones, or any combination thereof. Data system 370 is a system for viewing or making use of the collected data. Data system 370 may include a computing system, a display system, and/or a data storage system. Viewing system 270 is an example of data system 370. Data system 370 may be a single system or may be a distributed system spread across multiple geographic locations. Data hub 350 may transmit entire datasets to data system 370 or data system 370 may request or access specific subsets of data from data hub 350.

As illustrated in FIG. 3, smartphones 311 and 319 may also communicate directly with each other to exchange data. The communication between the smartphones may occur using wired or wireless communication methods. The participants may wish to share their data, or subsets of their data, with each other in addition to, or in place of, transmission of the data to data hub 350. In some situations, a software application running on one of the smartphones may enable the associated participant to request specific categories of data or data streams from another participant using either the direct path of communication or via data hub 350. Using a counterpart software application, a participant may have the option of granting or approving a request for data from another participant.

Data system 370 may be used by a coach, a virtual coach, a trainer, a virtual trainer, a doctor, a nurse, a physical therapist, a team captain, a spectator, a fan, a support crew, a statistician, an analyst, or a reporter. In addition, the data may also be used by a bettor that is placing a bet related to the event from which the data is being gathered or by another person performing a speculative activity related to the event (e.g., an insurer). The data may also be used by a sports equipment designer, a sports equipment manufacturer, or a sports equipment maintainer to design, improve, or maintain sports equipment. The data may also be used by any other party wishing to analyze or view information about a condition and/or the physical performance of one or more of the participants.

The performance characteristics or data may also be used for advertising or marketing purposes. In one example, advertisements may be targeted at the participants based on their condition or performance. This may occur during or after the event. In another example, marketing messages may be delivered to fans or spectators in a manner that is related to the performance characteristics being presented. In another example, a sponsor may deliver advertising messages that are specifically associated with the performance characteristics or metrics of individuals that they sponsor or individuals that use their product. In yet another example, various parties wishing to view the metrics or performance characteristics may be required to view one or more advertisements before getting access to the data.

In addition to providing processed data about the participants to data system 370, some or all of the processed data may be provided back to one or more of the smartphones. In one example, some or all of the data received from smartphone 311 by data hub 350 may be transmitted back to smartphone 311 in a post-processed form. This enables participant 305 have access to the data being produced by data hub 350 and provided to others. In another example, some or all of the post-processed data associated with participant 305 may be provided to participant 309, and/or vice versa. This allows participant 309 and/or participant 309's coaches to view or otherwise receive information about participant 309's condition or performance in real time, or near real time, during the event. This type of competitive data can be used to develop a strategy for the remainder of the event and may change the dynamics of the event in some cases.

Many types of data systems, viewing systems, or computing systems may receive data from data hub 350. The data may be owned and/or controlled by one business entity while the various users of the data may be associated with other entities. Therefore, an owner of data hub 350, or an owner of the data within data hub 350, may sell the data, sell access to the data, and/or a sell subscription to the data to various users. Data access may be sold or otherwise provided with pricing models having many different structures including pricing structures based on: amount of data, accuracy of data, resolution of data, lag time of data, number of participants, number of metrics, types of metrics, categories of metrics, comparisons to historical data, and/or combinations thereof. Many other types of data pricing models and structures are possible and the techniques disclosed herein are not to be limited to any particular model or structure.

Computer 380 is a computer that is owned or operated by participant 305 or someone associated with participant 305. Some or all of the data captured by smartphone 311 may also be transmitted to computer 380 for later use by participant 305 or someone associated with participant 305. The data may be transferred from smartphone 305 to computer 380 in real time as it is gathered, in near real time, or at some point later in time (e.g., after an event is completed). The data transferred to data hub 350 for sharing or distribution purposes may be a subset of the full data set participant 305 has available in smartphone 311 and/or is transferred to computer 380. The data may be transferred from smartphone 311 to computer 380 using wired, wireless, and/or optical communication methods. If significant data processing and/or complex algorithms are required, raw data may be sent from smartphone A to computer 380 and processed by computer 380, with some or all of the results of the processing being returned to smartphone A for display or use.

In some cases, participant 305 and participant 309 may be competing in an event that involves traversing a track or circuit multiple times. The track or circuit could be a running track, a length of a swimming pool, a series of roads, an auto race track, an ice rink, or any path that is traversed multiple times for purposes of exercise or competition. In this case, the various techniques described herein may be used to generate metrics on a 'per lap' basis. Traversing of a lap may be determined using GPS information, a gyroscope, an accelerometer, a camera, or a combination thereof. Traversing of a lap may also be determined using one or more devices placed in fixed locations along the course of the track. Mobile devices and/or sensors used by the participants may receive signals from the fixed devices as the participants pass by. Alternatively, the mobile devices and/or sensors used by the participant may transmit signals that are received by the fixed devices with that information being transmitted to a central processing hub, such as data hub 350.

When used in a competitive sport environment, the systems described herein may include features enabling officials of the event to verify proper operation of the devices and perform calibrations or other checks in order to verify that the data provided to data hub 350 is valid and/or accurate. Verifying proper operation may involve a number of different features or functions. In one example, data hub 350 may have the capability to command the smartphones to take a measurement from one or more of the sensors under known conditions in order to confirm that they are working properly and/or reporting valid data. In another example, participant 309 may requested to perform a warm up activity or physical motion in order to verify that the activity is being properly captured and reported by smartphone 319 and sensors 329. In yet another example, smartphone 311 and/or sensors 321 may include one or more biometric sensors, such as a retina scanning device, in order to verify the identity of participant 305. In another example, one or more of the devices in FIG. 3 may make use of a digital certificate, an identity certificate, a key certificate, or a similar type of electronic verification credential for determining that a device or participant is authorized to be using the system. The initial creation of the electronic verification credential may involve use of a certificate authority that is external to the illustrated systems. These processes may involve communication among data hub 350 and/or the smartphones and the certificate authority.

Individual sensors may also be subject to verification processes. In some situations, an individual sensor may also have a certificate or other type of credential. An individual sensor may also be calibrated based on a known input. The calibration of a sensor may be performed by the smartphone it is associated with or may be performed by a different computing device, such as computer 380. The calibration of a sensor may be performed in a different environment using equipment that is more controlled, accurate, and/or precise than the smartphone and other devices the sensor is associated with while in use.

Data hub 350 may also contain or communicate with a user interface (not pictured). This user interface may be used by an organizer of an event to manage what data is being captured and what data is being transferred between the various devices of FIG. 3 as well as to control or monitor the various other processes described herein.

In addition to the various configurations disclosed above, the apparatuses, systems, and methods described herein may also be implemented in a variety of other devices related to exercise and/or physical activity. Runners often use handheld drink bottles having hand straps making it easier for the runner to hold on to the bottle. The physiological sensors described herein may be implemented in a hand strap of this type of device to make reading from the back of the hand. The mobile electronic device to which the readings are transmitted may also be secured in the handheld device, in addition to or in place of the drink bottle, or may be held or located elsewhere on the runner's body. In one variation, the runner may carry and apparatus in each hand. Both apparatuses may contain sensors for improved measurement accuracy while one of the apparatuses carries the mobile electronic device and the other includes a drink bottle. These sensors may also be integrated into other items which are in contact with the back of the hand (e.g., a glove worn by a firefighter) or integrated into other items which are in contact with the activity participant (e.g., a piece of clothing worn by an athlete).

Figure 4:
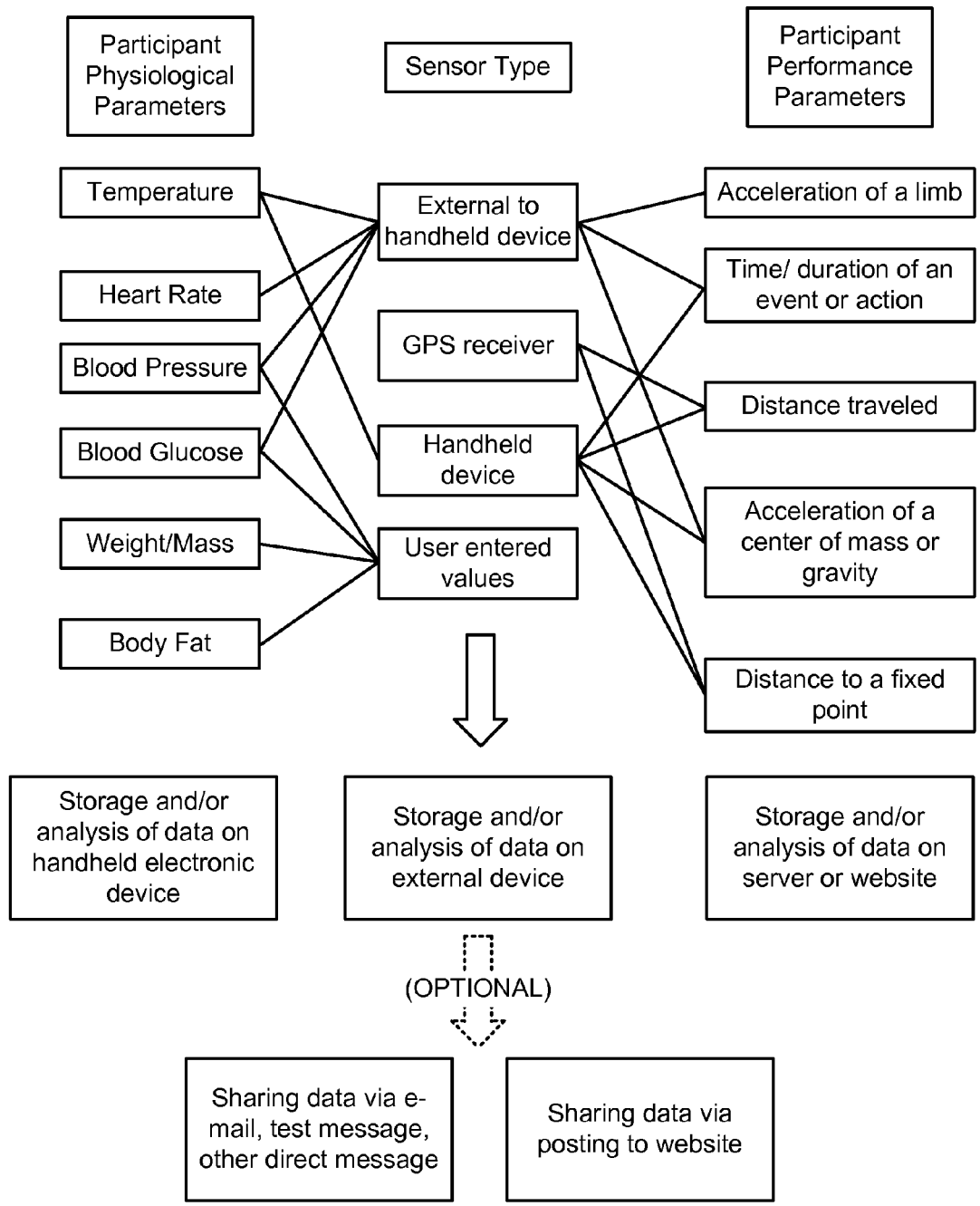
FIG. 4 is a data acquisition flow diagram in accordance with the techniques introduced here.

FIG. 4 illustrates some types of data that can be collected, processed, and disseminated using the techniques described herein. Each data type is indicated as collected by one or more types of sensors. The data from the sensors can be passed along or stored as shown, so that a participant can keep his or her performance statistics private or share the information with a coach, teammates, family, friends, club members, or the wider public through direct messages, postings, and the like.

Figure 5:
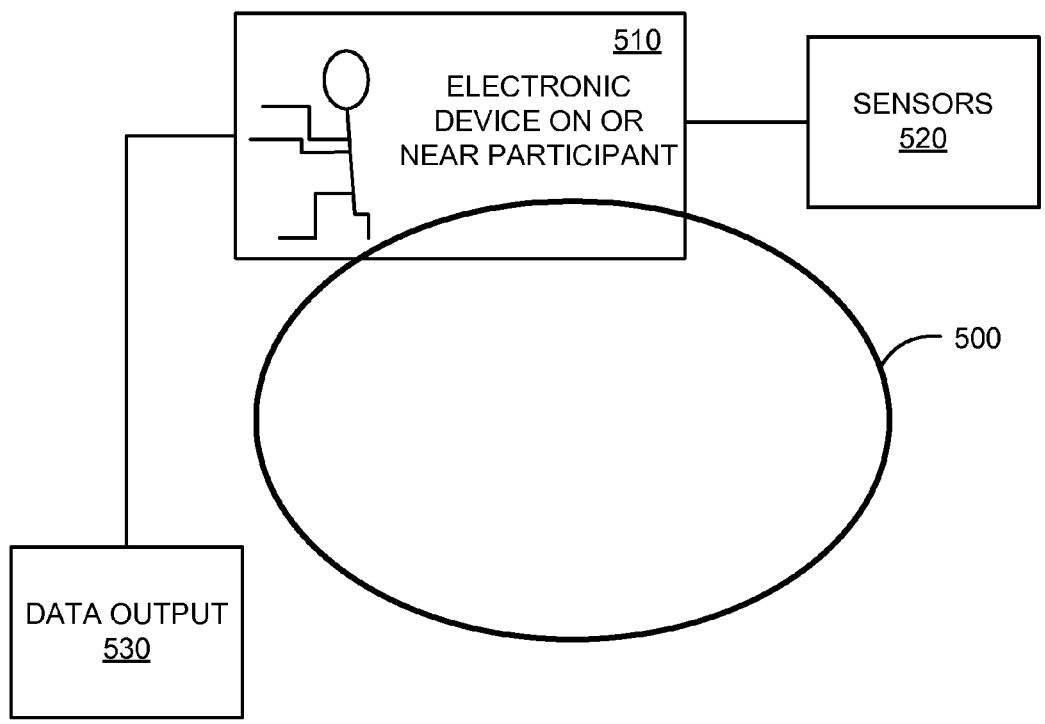
FIG. 5 is a schematic of information flows in a system in accordance with the techniques introduced here.

FIG. 5 illustrates an activity area 500 to show a data flow among one or more electronic devices 510 on or in proximity to a participant, sensors 520 on or near a participant, and data output devices 530, such as display or audio devices. The participant can be executing an activity on a course in the activity area 500. The participant can have one or more electronic devices 510, including hand held electronic devices, attached to his or her body, attached to a piece of equipment associated with the activity, or attached to his or her body and a piece of equipment. Electronic devices 510 can have inherent sensors 520, such as one or more accelerometers, gyroscopes, compasses, GPS receivers, timers, thermocouples, and the like. In addition to the inherent sensors associated with electronic devices 510, additional information may be obtained from sensors 520. Sensor 520 may be provided by the participant or may be provided by another party, such as an event organizer. Various types of sensors are discussed in greater detail hereinabove.

Electronic devices 510 can be ruggedized, such that they are water, dirt, dust, snow, crush, scratch, crush, and/or impact resistant. Electronic devices 510 can also be housed in a case or covering that renders it ruggedized. A participant can have special clothing that accommodates hand held electronic devices or mobile phones. Such clothing can have special pockets or compartments for holding or securing electronic devices 510. Electronic devices 510 and/or one or more other electronic devices can also be worn by a participant using a belt, band, pouch, or other accessory. A belt, band, or other accessory can have features suitable to the activity the participant chooses to engage in. Such features may include water, dirt, dust, snow, scratch, crush, and/or impact resistance. Such features may also include stabilizing features or mounting fixtures to attach electronic devices 510 to existing clothing or to an apparatus the participant may wear.

Additionally, the accessory can allow the participant to view the display of the electronic device, hear audio from the electronic device, or both view the display and hear audio while wearing the electronic device during an event or activity. The accessory can also allow a participant to optimally utilize certain inherent sensors, such as by positioning the electronic device on an extremity of a participant so that an accelerometer can calculate the full velocity of the extremity during an action, such as a golf stroke or baseball bat swing. Materials for the accessory can include those suited for rugged activities, such as light-weight, impact resistant polymers; neoprene; high strength polymer fabrics; composite materials, and metal alloys. An accessory can also be made of a quick-drying, light weight material, such as, but not limited to, Gore-Tex® and rip-stop nylon. Additionally, accessories normally worn by a participant can be modified to accommodate the electronic device. For example, a shoe or water bag that a participant would normally wear during a run could be modified to have a compartment or pouch for the electronic device.

Sensors within or on an electronic device can be in proximity to a participant, such as on a piece of equipment essential to the activity the participant is engaging in. Examples of equipment that an electronic device can be mounted on or housed within include a bicycle, a sports board, a scooter, a bench pressing bar, gym equipment, a golf club, a baseball bat, a piece of clothing, a helmet, a chest protector, and the like. Mounts for accommodating one or more electronic devices can be made of sufficiently strong, weight conscious, weather and impact resistant material. Such material may include light-weight metals, metal alloys, composite materials, polymers, ceramics, glasses, or any combination thereof. Sensors inherent or on an electronic device can be in proximity to a participant, such as on a device or apparatus, to track the motion of a participant closely enough to ascertain the desired data regarding his or her exertion. Such apparatus can include a boom, an arm, a dolly, a flexible mount, a screw-in mount, a pressure fit mount, and the like.

Sensors provided by an event organizer or used by a participant that are external to the hand held electronic device can be worn by the participant, mounted onto equipment used by the participant, positioned along a course used by the participant, or any combination thereof. A participant can wear additional sensors on extremities, such as the head, hands, arms, feet, or legs. Sensors worn on such locations can be worn as watches, on bands, on belts, as rings, as bracelets, as ear rings, as hair ties, on hats, on visors, on shoes or boots, or adhered directly to skin or clothing as an adhesive patch. Sensors can also be worn by a participant on his or her torso. When wearing sensors on the torso, a participant can use special shirts, belts, bands, sensors that are on adhesive patches, or any other suitable means to suitably place one or more sensors to obtain data without impairing the movement of the participant.

Sensors that are mounted on equipment can be mounted using adhesives, mounts that include grips, vices, clamps, laces, bolts, screw, clips, fasteners, Velcro®, or any combination thereof. Examples of equipment that a sensor can be mounted on or housed within include a bicycle, a sports board, a scooter, a bench pressing bar, gym equipment, a helmet, a chest protector, a race car, a golf club, a baseball bat, and the like. Mounts for accommodating one or more sensors can be made of sufficiently strong, weight conscious, weather and impact resistant material. Such material includes light-weight metals, metal alloys, composite materials, polymers, ceramics, glasses, or any combination thereof.

A course can be any location or venue a participant utilizes when involved in a physical activity. A course can be a track, including an elliptical track, a circular track, or an irregularly shaped track. Additionally, a course can include a lane on a track and field course, a lane in a swimming pool or other body of water, a running course, an obstacle course, a training circuit, a race track, a path along a street, a trail on land, a path along the shore of a body of water, a path between the shore of a body of water and a marker or buoy, a sports field, such as a baseball diamond or cricket field, and the like. Sensors can be located along a regular course to indicate that a participant has passed a certain point, completed a certain number of laps, or the like. For example, in a trail run or a marathon in a large city, race officials may wish to know that each participant adheres to the set course and that no short-cuts are taken. In addition, the time at which each participant passes each sensor can be used to generate a wide range of statistics with respect to an individual participant or among two or more participants relatively.

Sensors 520 can collect data and transmit that data to electronic devices. The participant can receive the data at electronic devices 510 in raw form. Alternately, the data may be processed before being transmitted to electronic devices 510. The data may also be communicated via a data output such as data output 530. Data output 530 may be, for example, a display on electronic devices 510 or speakers on electronic devices 510. Data may also be output to a website or application that is accessed using a computer or hand held electronic device, such as a smart phone or tablet computer. Data output 530 can also allow a coach, trainer, physician, spectator, or other observer to see, hear, or both see and hear data regarding a participant's performance and/or physical condition. Data outputs devices that can be accessed by other observers include score boards, large screen televisions or displays, audio streams, interactive displays on a computing device, interactive displays on a dedicated device, interactive displays on a handheld electronic device with an application that coordinates data presentation, websites, and the like.

The data output can be used to gauge relative performance of a participant with respect to earlier performances, with respect to idealized performance, with respect to a prediction, or with respect to a field of competitors. The field of competitors can be local, such that all competitors are on the same course, or the field of competitors can be scattered in various locations with similar facilities, or even scattered in time. After assessing a participant's performance, either instantaneous, projected, cumulative, or any combination thereof, the participant or an observer, such as a coach, may recommend or implement changes to alter the performance of the participant.

Electronic devices and/or sensors can exchange data with one or more other electronic devices. As such, an electronic device can act as a data aggregator for multiple devices and/or sensors.

In some implementations, the activity area 500 is a swimming pool, and the one or more electronic devices 510 can include a smart phone worn by a swimmer that is swimming in the swimming pool. The smart phone is preferably encased in a waterproof case that permits operation of the smart phone's controls and user interface via either a window in the case or by external buttons or switches or the like. The case may also provide other protective features, such as being shock or impact resistant. The one or more electronic devices 510 can be worn by a band, or in a specially-formed vest, suit, or belt. The one or more electronic devices 510 can be worn on the swimmer's wrist, lower arm, upper arm, waist, chest, back, leg, ankle, hands, feet, or head. In some situations, electronic devices 410 and or associated sensors may be positioned in specific physical locations for purposes of providing sensing and/or feedback related to that physical position. For example, an electronic device or sensor may be worn on the hand or wrist of a swimmer to gather data related to the swimmer's stroke. In another example, a sensor may be worn on or near the ear because certain physiological measurements may be more conveniently or more readily taken from the ear.

The one or more sensors 520 can include, without limitation, a heart rate monitor, a thermometer, a calorimeter, a location sensor such as a GPS device, a gyroscope, a speed sensor, a compass, an accelerometer a camera, a video camera, and/or a microphone. The one or more sensors 520 can also include one or more of a $VO_2$ sensor, a blood pressure monitor, an oxygen saturation monitor, a hemoglobin sensor, a blood flow sensor, a $CO_2$ monitor, a blood glucose sensor, a pulse oximeter, a breathing rate monitor, an electroencephalographic sensor, and/or an electrocardiographic sensor.

The data output 530 can include a distal handheld communication device, a television, a graphical display, a scoreboard, an alphanumeric display, a speaker, or set of speakers (such as wireless weatherproof speakers), or other output device. In some situations, data output 530 may also be a computing device and/or a communication network. For example, data output 530 may be a WiFi network or the Internet.

In some implementations, the combination of sensors 520 and electronic devices 510 can be configured to measure distance swum, strokes per length, strokes per unit time, kicks per length, kicks per unit time, instantaneous and/or average velocity, resistance in water, side to side motion during strokes or kicks, head pitch (head too low, too high), power expended, heart rate, $VO_2$, $VO_2$ max, lactic acid estimate, distance before hitting an object, and/or detection of kick/flip turns. In addition, sensors 520 and/or electronic device 510 may be configured to measure any of the other metrics described herein. In one example, when measuring a swimmer's progress in a pool, the location and velocity sensors can determine the swimmer's location and speed, and provide an alert to the swimmer when the swimmer is approaching a threshold distance from a wall or other barrier within the swimming pool.

In other implementations, the activity area 500 is a running track, and the one or more electronic devices 510 can include a smart phone worn by a runner that is running on the running track. The smart phone may be in a case that provides protection to the smart phone, but which still enables operation of the smart phone's controls and user interface via either a window in the case or by external buttons or switches or the like. The one or more electronic devices 510 can be worn by the runner via a band, or in a specially-formed vest, belt, or other apparel such as shorts or a shirt. The one or more electronic devices 510 and/or sensors 520 can be worn on the runner's wrist, lower arm, upper arm, waist, chest, back, leg, foot, or ankle. In other situations, the one or more electronic devices 510 and/or sensors 520 may be worn on the runner's hands, shoes, or head. In some situations, the specific positioning of the electronic device or sensor may be chosen to sense movement of a specific part of the body or appendage.

In some implementations, the combination of sensor(s) 520 and electronic device(s) 510 can be configured to measure stride length, foot falls per distance (steps per mile), strides or foot falls per minute, side to side motion of the upper body, instantaneous changes in velocity (including with respect to altitude, incline, period in race, etc.), heart rate, temperature, force on feet/limbs, $VO_2$, $VO_2$max, lactic acid build-up estimate, energy exertion, power exertion by either or both of the runner's legs, etc. The measurements can also yield information as to tendencies of a runner to favor one side/foot over the other, irregular gait, variations in speed or accelerations, comparisons of information based on time of day and/or food consumption, and other determinations.

In yet other implementations, the activity area 500 is a bicycle track, such as a velodrome or a track, and the one or more electronic devices 510 can include a smart phone worn by a bicyclist that is cycling on the bicycle track. The smartphone may be in a protective cover that permits operation of the smart phone's controls and user interface via either a window in the case or by external buttons or switches or the like. The one or more electronic devices 510 can be worn by the bicyclist via a band, or in a specially-formed vest, belt, or other apparel such as shorts or a shirt. The one or more electronic devices 510 and/or sensor 520 can be worn on the bicyclist's hands, wrist, lower arm, upper arm, waist, chest, back, leg, foot, ankle, clothing, or shoes. Further, the one or more electronic devices 510 can be mounted to a bicycle, to a helmet, or to other equipment of the bicyclist. For instance, the one or more electronic devices 510 can be mounted on handle bars, pedals, wheels, or frame of the bicycle.

In some implementations, the combination of sensor(s) 520 and electronic device(s) 510 can be configured to measure number of pedal cycles per unit time, per unit distance, heart rate, temperature, $VO_2$, $VO_2max$, lactic acid estimate, power expenditure, force on feet/knees, swaying side to side during ride, wind resistance of the bicyclist. Any of these characteristics may be measured and determined either in an instantaneous manner or over a predefined period of time (e.g., during an event).

In still yet other implementations, the activity area 500 can be any type of sports venue, such as a hockey rink, a boxing ring, a football field, a golf course, a baseball diamond, a soccer field, a rugby field, a field hockey field, a tennis court, a squash court, a racquetball court, an ocean, or a lake. Other activity areas are possible. A combination of sensor(s) 520 and electronic device(s) 510 can be configured to measure various types of physical or physiological data pertaining to a participant's participation in an event related to the activity area 500, and provide information and data to a data output 530. For instance, the sensors 520 can measure the speed of a hockey player or the force of a hockey stick. The sensors 520 can measure a velocity of a boxing glove and/or the force of a punch. The sensors 520 can measure progress of a golfer as the golfer performs each golf swing, as well as metrics attendant to the game of golf, such as heart rate, body temperature, time of day, outside temperature, or the like. Those having skill in the art would recognize that electronic devices 510 worn by, or in near proximity to a participant of an event, in combination with one or more sensors 520, can measure various types of physical or physiological data pertaining to the event or the participant's participation in the event, and process the measurements to generate a data output 530 to provide a useful representation of the characteristics. These representations can be further processed for trends, maximums, minimums, or other key performance information for further evaluation and feedback.

Figure 6:
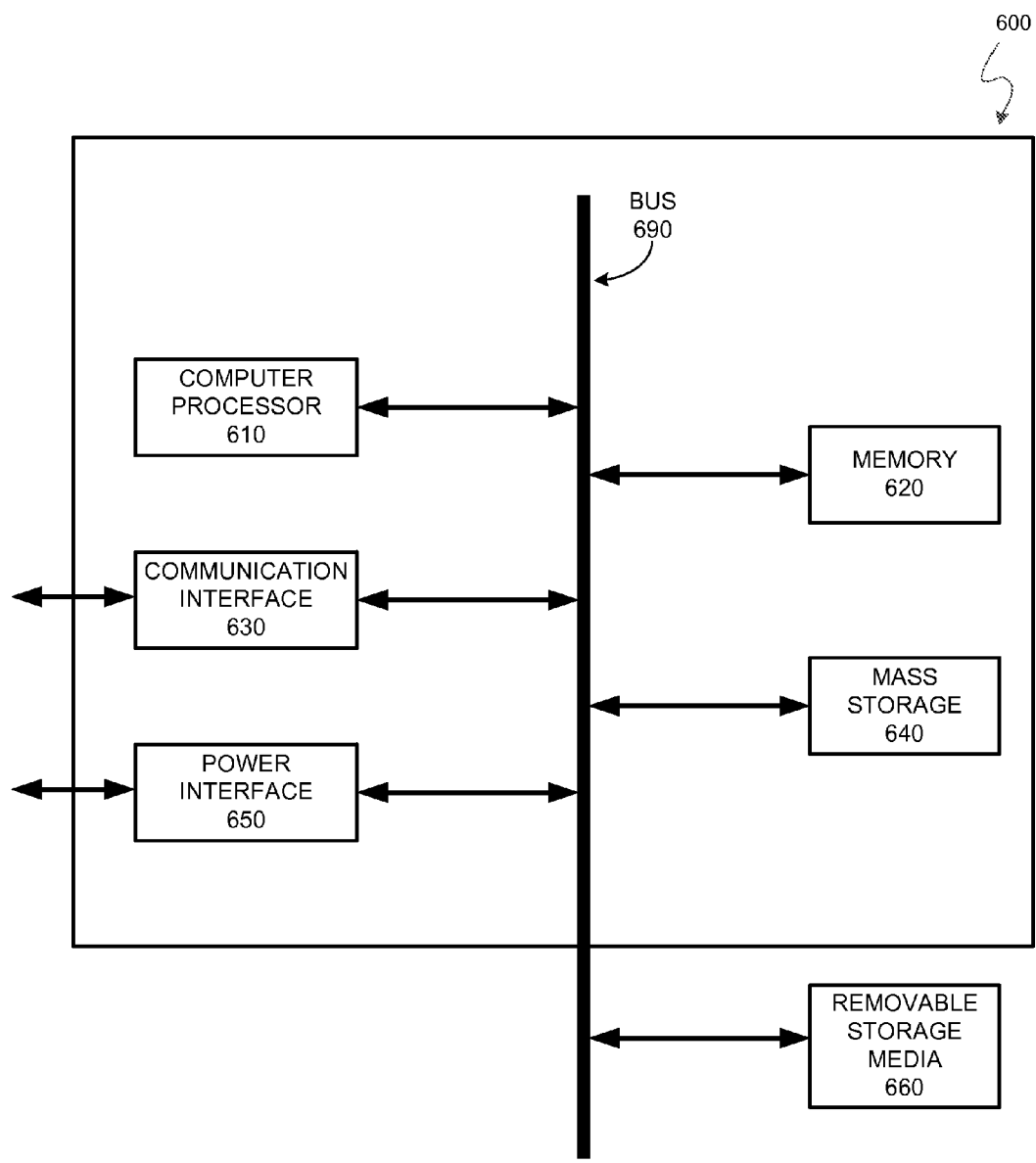
FIG. 6 illustrates a computer system with which some of the disclosed techniques may be implemented.

FIG. 6 illustrates computer system 600 with which some embodiments of the techniques disclosed herein may be implemented or utilized. Computer system 600 includes a bus 690, at least one computer processor 610, at least one communication interface 630, at least one memory 620, at least one mass storage device or module 640, and at least one power interface 650. A removable storage media 660 may also interface to bus 690 of computer system 600.

Computer processor 610 can be any known computer processor, central processing unit, microprocessor, microcontroller, programmable logic array, and/or programmable logic device. Computer processor 610 may also interface to a coprocessor.

Communication interface 630 can be any type of interface for communicating with another device or a network over a communication link or over a communication channel. Communication interface 630 may be configured for communicating using a wired connection, a wireless connection, audio signals, light waves, IR, or a combination thereof. Communication interface 630 may be configured for communicating with or over a network such a Local Area Network (LAN), Wide Area Network (WAN), or any network to which computer system 600 connects. Communication interface 630 may also be configured to communicate with an electronic device such as a cellular phone, a smartphone, a tablet, a laptop computer, a server, or a digital audio device. The various functions of communication interface 630 may be distributed across multiple communication interfaces.

Memory 620 can include random access memory (RAM), or any other type of dynamic data storage device commonly known in the art. Memory 620 may also include one or more static storage devices such as read only memory (ROM), programmable read only memory (PROM), flash memory, magnetic memory, erasable programmable read only memory (EPROM), and/or electrically erasable programmable read only memory (EEPROM) for storing static data such as firmware or machine-executable instructions for computer processor 610 or for another computer processor.

Mass storage 640 can include one or more persistent mass data storage devices or modules that may be used to store data, information, and/or instructions. Mass storage 640 may include a hard drive, a tape drive, an optical drive, flash memory, a micro electromechanical storage device, or a combination thereof.

Power interface 650 can be any type of interface for receiving and/or transmitting electrical power. The functions of power interface 650 may be spread across multiple power interfaces. Power interface 650 may include a battery and may interface to external devices for purposes of charging the battery. The functions of power interface 650 may also be combined into a single connector and/or interface with communication interface 630. For example, the functions of communication interface 630 and power interface 650 may both be implemented in the form of one or more USB interfaces.

Removable storage media 660 can be any kind of external data storage device including a hard drive, a memory card, a subscriber identity module (SIM) card, flash memory, an optical drive, a tape drive, a micro electromechanical storage device, or a combination thereof.

Bus 690 communicatively couples the elements of computer system 600, as well as removable storage media 660. Bus 690 may conform to an industry standard bus architecture and protocol or may use a proprietary architecture and/or protocol.

Sensor 120, sensors 220, sensors 321, sensors 329, and/or sensors 520 may include computer system 600 or one or more elements of computer system 600. A sensor package or assembly may include one or more of these components in order to perform conditioning, normalizing, biasing, filtering, attenuating, adjusting, converting, averaging, or some other type of processing on measurement made from one or more sensors. A sensor package may also include a power source, such as a battery, for powering one or more of the components.

One or more of the sensors or associated circuitry may be operated according to a duty cycle in order to preserve power and increase the operational life of the device before recharging or battery replacement is necessary. Although a power saving mode may reduce accuracy to some extent because measurements are not being made as frequently or during some periods of time, the duty cycle may be intelligently adjusted based on operational conditions in order to reduce any adverse effects of applying the duty cycle. For example, when one or more measured parameters, such as a heart rate, are relatively stable, the "on" state of the duty cycle may be proportionally decreased without losing significant accuracy or resolution. When a larger change in the measured parameter relative to one or more previous measurements is detected, the duty cycle may be adjusted to make more frequent measurement of the changing parameter.

In another example, the duty cycle may be adjusted based on geographical information about an exercise course and/or historical information about how a user has performed on that course in the past. If the user is cycling through a relatively easy section of a course and/or typically has stable physiological conditions in that portion of the course, measurement frequency may be reduced in order to preserve battery life for portions of the course in which more frequent measurements will provide more meaningful or useful data. Similarly, measurement of one or more environmental conditions may be performed at lower frequencies or with lesser duty cycles when the condition is not near a critical threshold. For example, air quality measurements may be made relatively infrequently when the measurements indicate that the air quality is well within an acceptable range, but the measurement frequency may be increased if the measurements begin to show significant changes in the air quality and/or if the air quality is near a threshold or limit of interest.

Figure 7:
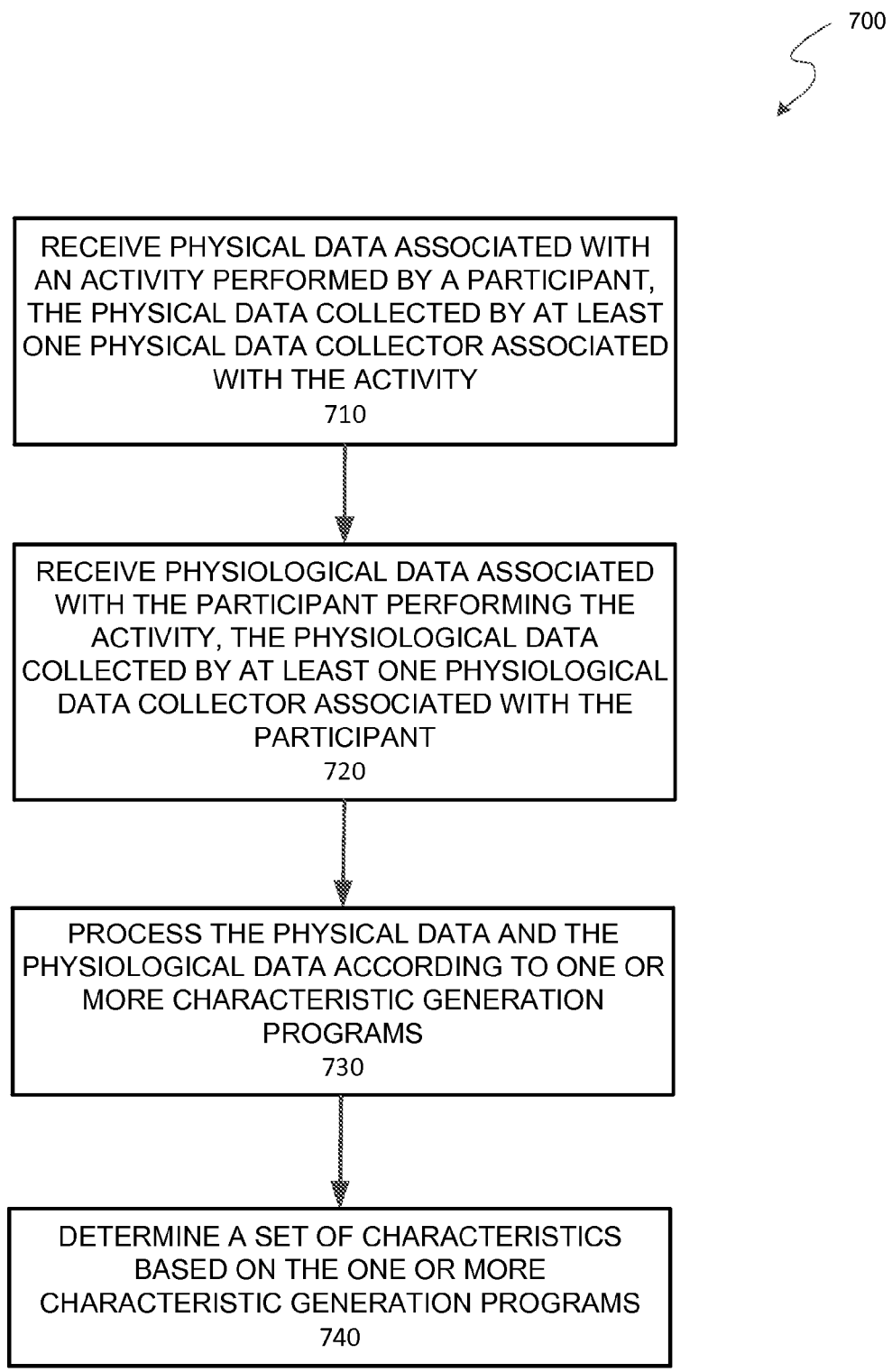
FIG. 7 illustrates a method of determining a set of characteristics of a participant performing an activity.

FIG. 7 illustrates method 700 of determining a set of characteristics of a participant performing an activity. Method 700 may be performed by one or more computer processors, such as computer processor 610, of an electronic device, such as mobile device 110, mobile device 210, smartphone 311, smartphone 319, and/or electronic device 510. At step 710, method 700 includes receiving physical data associated with an activity performed by a participant, the physical data being collected by at least one physical data collector associated with the activity. At step 720, method 700 includes receiving physiological data associated with the participant performing the activity, the physiological data being collected by at least one physiological data collector associated with the participant. At step 730, method 700 includes, processing the physical data and the physiological data according to one or more characteristic generation programs. Finally, at step 740, method 700 includes determining a set of characteristics based on the one or more characteristic generation programs.

In some cases, method 700 may include generating a graphical representation of the set of characteristics and transmitting the graphical representation over a communication network, such as network 290, to one or more recipient devices, such as data processing system 250, viewing system 270, or data system 370. Many other variations of method 700 are possible using the various techniques disclosed herein. The methods and other techniques disclosed herein may be performed by the one or more computer processors through execution of computer readable instructions configured in the form of a software program or a software application (e.g., an app).

Figure 8:
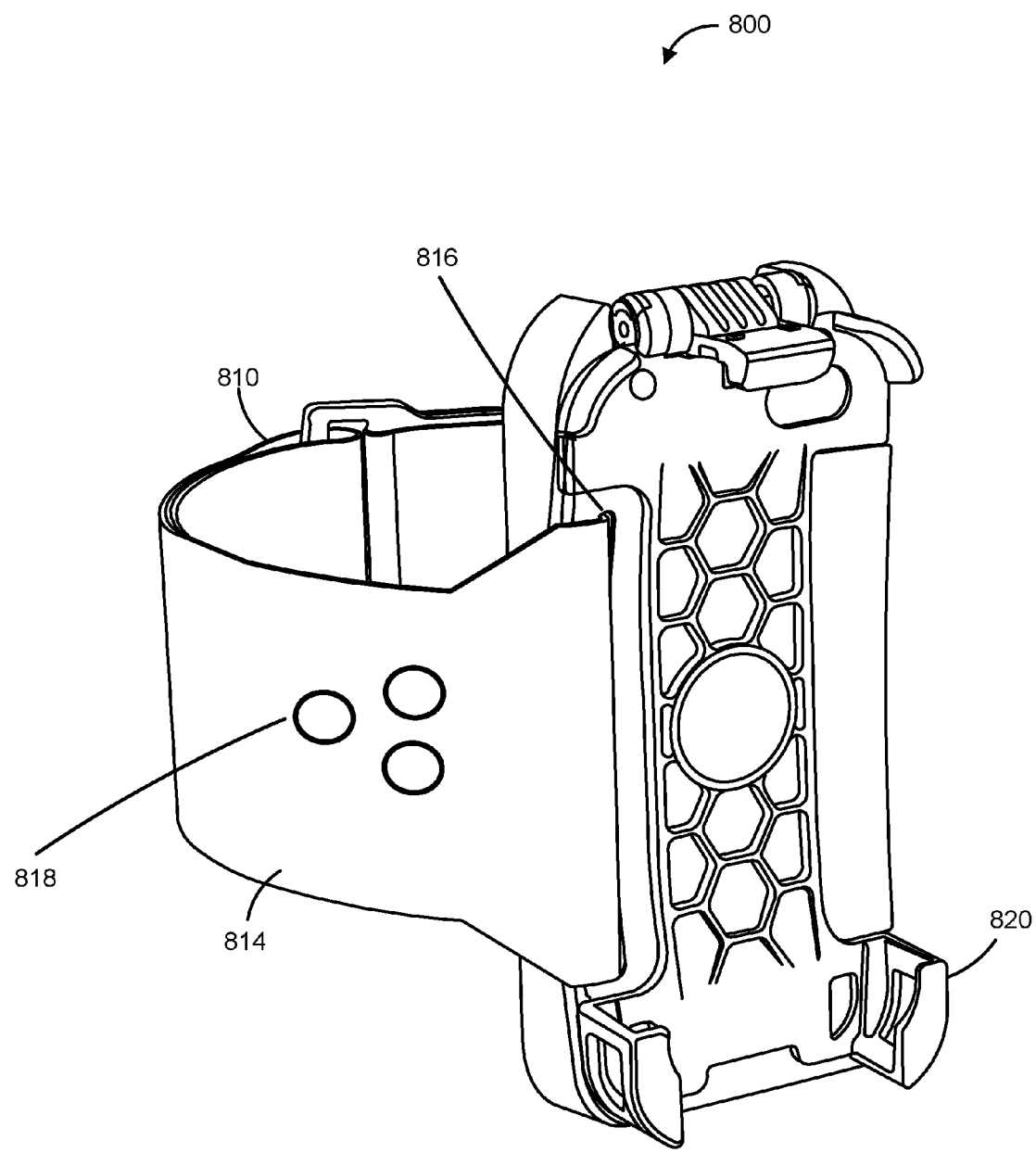
FIG. 8 illustrates a system including a protective case for a mobile electronic device and an armband.

FIG. 8 illustrates a system 800 including a protective case 820 for a mobile electronic device (not pictured). System 800 includes an armband or strap, such as armband 810. Protective case 820 may have many different configurations and may cover part or all of the mobile electronic device. Armband 810 includes an elastic member 814 for removably attaching the armband to an arm of a person. Armband 810 and/or protective case 820 include one or more clasping mechanisms, such as clasping mechanism 816, for securing the armband 810 to protective case 820. In some instances, armband 810 may include one or more input device(s) such as buttons 818. In some instances, armband 810 may include a feedback device, such as a haptic feedback device and/or feedback device(s) 228. In some instances, armband 810 and/or protective case 820 may contain sensor(s), such as sensor(s) 220, and/or electrical circuitry, such as any of the components of computer system 600.

The apparatuses, devices, systems, and methods described herein may be implemented in a wide variety of configurations and with respect to a wide variety of physical activities. Descriptions of several additional implementations follow. However, the scope of the techniques introduced here is not to be limited to or limited by an of these example implementations.

In one example, a woman who is hypertensive is instructed by her physician to monitor her blood pressure and to aim for 30 minutes of moderate physical activity at least 4 times a week. The woman uses a blood pressure monitor to track her blood pressure daily, and enters such data via the blood pressure monitor or manually into an application (e.g., an app) on her smart phone. Her smart phone has a timer and is able to connect to a heart rate monitor that she wears while exercising. The timer and heart rate monitor record her duration and exertion levels while exercising, and this data is stored on the woman's smart phone. This data is recorded on the smart phone, and prior to her regular doctor's visits, the woman reviews the data to see whether her blood pressure is lowering or within a desirable range. The data can also be sent to the woman's physician for entry into her medical records.

In another example, a participant is a male runner who regularly trains for long-distance races, such as marathons. The runner has a pedometer that is calibrated for his stride length, such that if he does not alter his gait, a known number of strides are equivalent to a unit distance (e.g., a mile or kilometer). The runner wears this pedometer, wears a heart rate monitor, and affixes his handheld electronic device to the same location on his body with each run. The handheld electronic device includes, among other things, a timer, a clock, a GPS receiver, and one or more accelerometers. The pedometer and heart rate monitor relay data to the handheld electronic device. Other data that may be gathered includes data relating to distance, number of footfalls per unit distance or time, exertion, time, location, and relative motion. This agglomeration of data is recorded on the handheld device using one or more software applications, and may be transferred to a remote location or another device. The runner can monitor gait and body position over the course of a circuit of a track or running course. The runner can also monitor his speed, acceleration, and exertion during a specific run or over the course of his training cycle. His data can be shared with coach or with a running club, if he so chooses.

A female cyclist is the subject of another example. The woman combines a heart rate monitor and an external GPS receiver with features of her handheld electronic device, which is a multi-media device that has a camera, one or more accelerometers, clock, and timer. The woman regularly cycles on a track or trail of known length, and she monitors the time it takes to complete a lap or circuit. She also monitors her exertion, as measured by the heart rate monitor; the variations in her side to side motion as she propels herself forward; differences in her leg strokes downwards on the gears of her bicycle; the stroke or downward motion of each leg per minute or circuit; and the variations in her center of gravity, as indicated by the location of her multimedia device which is affixed consistently in a location near her center of gravity. All of this data is stored on the woman's device in one or more applications, and may be transferred to a remote location or another device. Her data can be shared with coach, cycling club, teammates, family, friends, or the wider public, if she so chooses.

A male swimmer is presented in another example. The man has a heart rate monitor that he wears as he swims. His smart cell phone, or smartphone, is encased in a waterproof case that is affixed to his chest, along his mid-line. The smart cell phone has one or more accelerometers, a GPS receiver, a time, a clock, a camera with a visible and/or IR sensor, and the ability to communicate with the heart rate monitor as well as external motion sensors that the man wears on his wrists and ankles. The man trains in a swimming pool of known dimensions, but on occasion will compete or train in a new environment. The camera of the smart cell phone can be used to estimate the distance remaining to a predetermined, fixed item or location, so that this data in combination with a time marking sensor, can determine the swimmer's speed and other statistics during a circuit of the pool or swimming environment. The GPS receiver may be used in a similar capacity to monitor the distance swam by the man and his speed.

Motion detectors worn by the swimmer and the accelerometers in his cell phone generate data that can indicate his side to side motion as he propels himself forward through the water, strokes per minute or lap, the relative pull of each arm stroke, the relative push of each kick, and the rhythm of his strokes. The heart rate monitor helps to indicate the exertion of the swimmer during a swim, as well as over many training sessions. The swimmer's data is recorded on his smart cell phone in one or more applications, and may be transferred to a remote location or another device. His data can be shared with coach, swimming club, teammates, family, friends, or the wider public, if he so chooses.

In yet another example, a handheld electronic device for determining characteristics pertaining to a participant's participation in an event is provided. The handheld electronic device may include a processor, two or more data collectors, and a memory. The two or more data collectors may be selected from a group consisting of: a clock, a timer, a stop watch, a motion sensor, a speed sensor, a pedometer, a cadence sensor, an accelerometer, a power meter, a mass sensor, an inertia sensor, a wind resistance sensor, a rolling resistance sensor, a pressure sensor, a strain gauge, a heart rate monitor, a thermal sensor, a compass, a magnetic sensor, a gravity sensor, a gyroscope, a GPS receiver, a compass, an altitude sensor, a humidity sensor, an acoustic sensor, and a photo detector sensor. Other data collectors or data sensors are possible.

The memory may store one or more application programs that, when executed by the processor, determine one or more of the characteristics based on data collected from the two or more data collectors. The characteristic to be determined by the handheld electronic device in the example above may be one or more of time, distance, speed, acceleration, power, efficiency, heart rate, calories consumed or ingested, calories burned, energy expended, temperature, lap time, laps per minute, total laps, reps per minute, total reps, position, or orientation.

In another example, a method of automatically determining the time it takes a participant to perform one or more laps of a circuit is provided. The method may include using a handheld device to determine a position of the participant, using the handheld device to determine a direction of travel on the circuit, using the handheld device to determine a distance to be traveled in the circuit, and using the handheld device to calculate the amount of time it takes to travel the distance. The method may be performed using one or more of the devices discussed above. In some cases, the distance to be traveled may be entered directly into the handheld device or selected from a menu of preselected options.

The methods discussed above may also include: determining a number of strides taken per lap, a number of strides per minute, speed in completing one or more laps, gait, determining relative weight distribution between a left stride and a right stride, relative force of impact exerted between a left stride and a right stride, timing of footfalls, sideways translation versus forward progression, and foot position during each stride, the amount of calories burned per mile, total calories burned by said participant, the total energy expended by the participant, the power expended by the participant, efficiency, body temperature, cadence, total revolutions of a bicycle crank set, weight distribution, relative weight distribution between a left pedal stroke and a right pedal stroke, relative down force between the left pedal stroke and the right pedal stroke, side-to-side motion versus forward motion, a location of the participant's center of gravity, and calories burned per unit distance traversed.

In some cases, the handheld electronic device is waterproof or is contained in a waterproof case. In these situations, the device may be used in a pool or body of water by a swimmer. The device may be used to determine characteristics such as: the time required to traverse a lane of the pool, the total distance traveled, the number of strokes per lap, strokes per minute, speed in completing one or more laps, relative weight distribution between a left stroke and a right stroke, a relative force exerted between a left stroke and a right stroke, a location of the participant's center of mass, or a relative torsion or side-to-side motion versus forward motion. The device may also be used to perform an analysis of the swimmer's rotations.

Some or all of the steps and operations associated with the techniques or methods introduced here may also be performed by hardware components or may be embodied in non-transitory machine-executable instructions that cause one or more general purpose or special purpose computer processors programmed with the instructions to perform the steps. The machine-executable instructions may be stored on a computer-readable or machine-readable medium. The steps may be performed by a combination of hardware, software, and/or firmware. In some cases the machine-executable instructions may be downloaded from a server, from a website, and/or from an application store or an app store.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods, apparatuses, devices, and systems are described herein in detail with reference to certain versions, it should be appreciated that other versions, methods of use, embodiments, and combinations thereof are also possible. Therefore, the spirit and scope of the appended claims should not be limited to the description of the embodiments contained herein.

The phrases "in some embodiments," "according to some embodiments," "in the embodiments shown," "in other embodiments," "in some examples," "in some cases," "in some situations," "in some configurations," "in another configuration," and the like, generally mean that the particular feature, structure, or characteristic following the phrase is included in at least one embodiment of the present invention and/or may be included in more than one embodiment of the present invention. In addition, such phrases do not necessarily refer to the same embodiments or different embodiments.

What is claimed is:

1. A system comprising:
   a protective case configured for use with a mobile electronic device, the protective case configured to enclose at least a portion of the mobile electronic device when the mobile electronic device is installed in the protective case; and
   an armband including:
      a clasping mechanism configured to secure the protective case to the armband;
      an elastic member configured to removably secure the armband to an arm of a participant performing an activity;
      a physiological data sensor configured to collect physiological data associated with the participant performing the activity;
      an equipment sensor configured to collect equipment data from a piece of sports equipment;
      electrical circuitry configured to receive the physiological data from the physiological data sensor, receive the equipment data from the equipment sensor, and wirelessly transmit the physiological data and the equipment data; and
      a haptic feedback device configured to provide haptic feedback to the participant based on the received physiological data and equipment data, wherein the haptic feedback device is configured to vary a characteristic of the haptic feedback based on the received data.

2. The system of claim 1 wherein the armband further includes a motion sensor configured to collect motion data and wherein the electrical circuitry is further configured to process the physiological data to remove motion artifacts from the physiological data, based on the motion data, before the physiological data is transmitted to the installed mobile electronic device.

3. The system of claim 1 wherein the armband further includes one or more buttons accessible by the participant, the electrical circuitry further configured to detect activation of the one or more buttons and wirelessly transmit an indication of a detected activation of the one or more buttons to the installed mobile electronic device.

4. The system of claim 1 wherein the varied characteristic of the haptic feedback is varied based on the physiological data.

5. The system of claim 1 wherein the varied characteristic of the haptic feedback includes a frequency of the haptic feedback that is varied based on the physiological data.

6. The system of claim 1 wherein the varied characteristic of the haptic feedback includes a duration of the haptic feedback that is varied based on the physiological data.

7. The system of claim 1 wherein the physiological data sensor comprises:
   one or more optical energy sources configured to direct optical energy toward skin of the participant; and
   one or more optical detectors configured to detect a portion of the optical energy reflected from the skin.

8. The system of claim 1 further comprising an environmental data sensor configured to collect environmental data from an area near the participant.

9. The system of claim 1 wherein the electrical circuitry is further configured to determine a subset of at least one of the physiological data and the equipment data based on a data sharing option selected by the participant.

10. The system of claim 9 wherein the electrical circuitry is further configured to transmit the determined subset of the at least one of the physiological data and the equipment data for delivery to a second mobile electronic device.

11. The system of claim 10 wherein the transmission for delivery to the second mobile electronic device occurs on a time delayed basis relative to the transmitting of the physiological data and the equipment data to the installed mobile electronic device.

12. A system comprising:
   a protective case configured for use with a smartphone; and
   an armband including:
      a clasping mechanism configured to removably secure the protective case to the armband;
      an arm strap configured to removably secure the armband to an arm of a participant performing an activity;
      two or more sensors configured to collect data associated with the participant performing the activity;
      a computer processor configured to:
         receive the data from the two or more sensors and wirelessly transmit the data; and
         determine a subset of the data based on a user input and wirelessly transmit the subset of the data over a network for delivery to an electronic device, wherein the subset of the data is transmitted on a time delayed basis relative to the transmitting of the data for delivery to the smartphone; and
      a haptic feedback device configured to provide haptic feedback to the participant based on the collected data, wherein the haptic feedback device is configured to vary an amplitude or duration of the haptic feedback based on the collected data.

13. The system of claim 12 wherein the two or more sensors include:
   two or more optical energy sources configured to direct optical energy toward skin of the participant; and
   one or more optical detectors configured to detect a portion of the optical energy reflected from the skin.

14. The system of claim 12, the armband including a volume increase button, a volume decrease button, and a mute button, wherein the computer processor is configured to detect activation of one or more of the buttons and wirelessly transmit a button activation signal for delivery to the smartphone.

15. The system of claim 12 wherein the two more data sensors comprise a physiological data sensor and an equipment sensor, the equipment sensor removably attachable to a piece of sports equipment.

16. The system of claim 12 wherein the two more data sensors comprise a physiological data sensor and an environmental sensor.

* * * * *